(12) United States Patent
Lujan et al.

(10) Patent No.: US 9,427,147 B2
(45) Date of Patent: Aug. 30, 2016

(54) DIRECTIONAL OPTICAL COHERENCE TOMOGRAPHY SYSTEMS AND METHODS

(71) Applicants: The Regents of the University of California, Oakland, CA (US); The Medical College of Wisconsin, Inc., Milwaukee, WI (US)

(72) Inventors: Brandon Lujan, Berkeley, CA (US); Austin Roorda, El Cerrito, CA (US); Joseph Carroll, Milwaukee, WI (US); Carlos Rivera-Carpio, San Francisco, CA (US); Vikram Makhijani, Vallejo, CA (US)

(73) Assignees: The Regents of the University of California, Oakland, CA (US); The Medical College of Wisconsin, Inc., Milwaukee, WI (US)

( * ) Notice: Subject to any disclaimer, the term of this patent is extended or adjusted under 35 U.S.C. 154(b) by 105 days.

(21) Appl. No.: 14/378,083

(22) PCT Filed: Feb. 15, 2013

(86) PCT No.: PCT/US2013/026491
§ 371 (c)(1),
(2) Date: Aug. 11, 2014

(87) PCT Pub. No.: WO2013/123430
PCT Pub. Date: Aug. 22, 2013

(65) Prior Publication Data
US 2015/0015846 A1    Jan. 15, 2015

Related U.S. Application Data

(60) Provisional application No. 61/600,495, filed on Feb. 17, 2012.

(51) Int. Cl.
*A61B 3/14*    (2006.01)
*A61B 3/00*    (2006.01)
*A61B 3/10*    (2006.01)

(52) U.S. Cl.
CPC .............. *A61B 3/0075* (2013.01); *A61B 3/102* (2013.01); *A61B 3/14* (2013.01)

(58) Field of Classification Search
CPC .......... A61B 3/102; A61B 3/12; A61B 3/14; A61B 2019/5234; A61B 5/0073; A61B 3/1025; A61B 3/112; A61B 3/11; A61B 3/13
USPC ................................ 351/206, 246, 221, 205
See application file for complete search history.

(56) References Cited

U.S. PATENT DOCUMENTS 5,537,162 A    7/1996    Hellmuth et al.
5,943,117 A    8/1999    Van De Velde
(Continued)

FOREIGN PATENT DOCUMENTS

FR    2973997 A1    10/2012

OTHER PUBLICATIONS

Gao et al. "Measuring retinal contributions to the optical Stiles-Crawford effect with optical coherence tomography", Optics Express, 16(9), Apr. 28, 2008, 6486-6501.
(Continued)

*Primary Examiner* — Hung Dang
(74) *Attorney, Agent, or Firm* — Rudy J. Ng; Bret E. Field; Bozicevic, Field & Francis LLP

(57) ABSTRACT

An optical coherence tomography system that includes an optical device having an adjustable optical element configured to displace a pupil entry point of light is provided. Optical coherence tomography methods using the optical coherence tomography system are also provided. The subject optical coherence tomography systems and methods find use in a variety of different applications, including imaging applications.

20 Claims, 20 Drawing Sheets

(56) References Cited

U.S. PATENT DOCUMENTS

| | | |
|---|---|---|
| 7,145,661 B2 | 12/2006 | Hitzenberger |
| 7,835,010 B2 | 11/2010 | Morosawa et al. |
| 2001/0000124 A1 | 4/2001 | Kollin et al. |
| 2004/0109135 A1 | 6/2004 | Watanabe et al. |
| 2006/0114411 A1 | 6/2006 | Wei et al. |
| 2010/0097573 A1 | 4/2010 | Verdooner et al. |
| 2010/0265511 A1 | 10/2010 | Izatt |
| 2011/0090509 A1 | 4/2011 | Bednarczyk et al. |
| 2011/0101207 A1 | 5/2011 | Schmitt |
| 2012/0092616 A1 | 4/2012 | Peyman |
| 2012/0274897 A1 | 11/2012 | Narasimha-Iyer et al. |
| 2013/0265547 A1* | 10/2013 | Higuchi ............ A61B 3/152 351/208 |

OTHER PUBLICATIONS

Guedes et al. "Optical coherence tomography measurement of macular and nerve fiber layer thickness in normal and glaucomatous human eyes", Ophthalmology, Jan. 2003, 110(1), 177-189.

Hee et al. "Topography of diabetic macular edema with optical coherence tomography", Ophthalmology, Feb. 1998, 105(2), 360-370.

Hee et al. "Optical Coherence Tomography of the Human Retina", Arch. Ophthalmol., Mar. 1995, 113(3), 325-332.

Huang et al. "Optical coherence tomography", Science, vol. 254, No. 5035, Nov. 22, 1991, 1178-1181.

Izatt et al. "Micrometer-Scale Resolution Imaging of the Anterior Eye In Vivo With Optical Coherence Tomography", Arch Ophthalmol. 1994, 112(12), 1584-1589.

Lujan et al. "Revealing Henle's Fiber Layer Using Spectral Domain Optical Coherence Tomography", Investigative Ophthalmology Visual Science (IOVS), Mar. 2011, 52(3), 1486-1492.

Otani et al. "Improved Visualization of Henle Fiber Layer by Changing the Measurement Beam Angle on Optical Coherence Tomography", Retina, J. Retinal & Vitreous Diseases, 2011, vol. 31, No. 3, 497-501.

Pierre and Marie Curie University (UPMC): "A Device and Method to Aid in the Detection of the Anatomical Features of Tissue", Technology Offer, Corporate Partnerships and Technology Transfer Office (DGRTT), Nov. 2011, 1 page.

Puliafito et al. "Imaging of macular diseases with optical coherence tomography", Ophthalmology, 1995, 102(2), 217-229.

Schuman et al. "Quantification of Nerve Fiber Layer Thickness in Normal and Glaucomatous Eyes Using Optical Coherence Tomography: A Pilot Study", Arch Ophthalmol. 1995, 113(5), 586-596.

* cited by examiner (a)

(b)

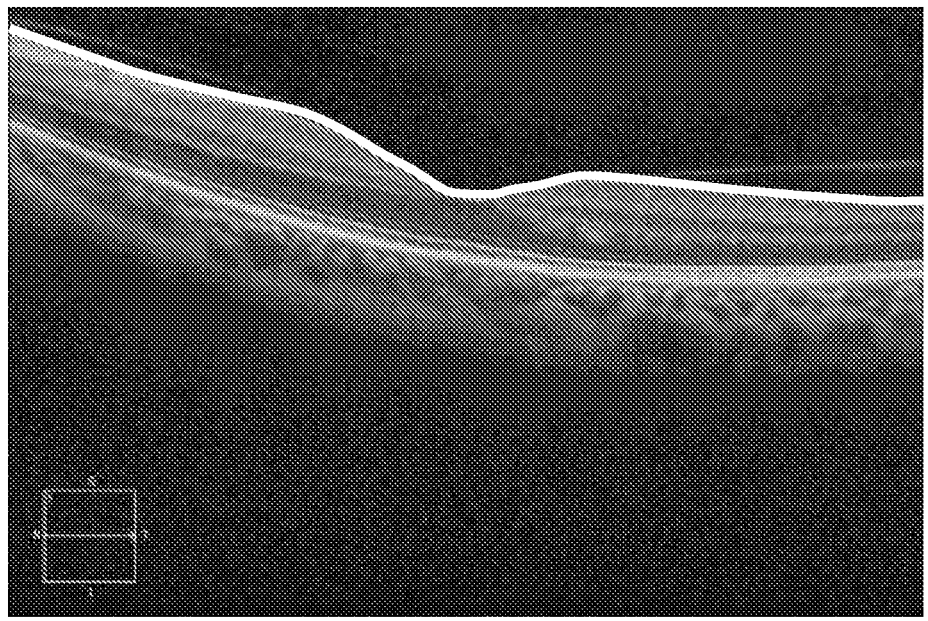
(c)
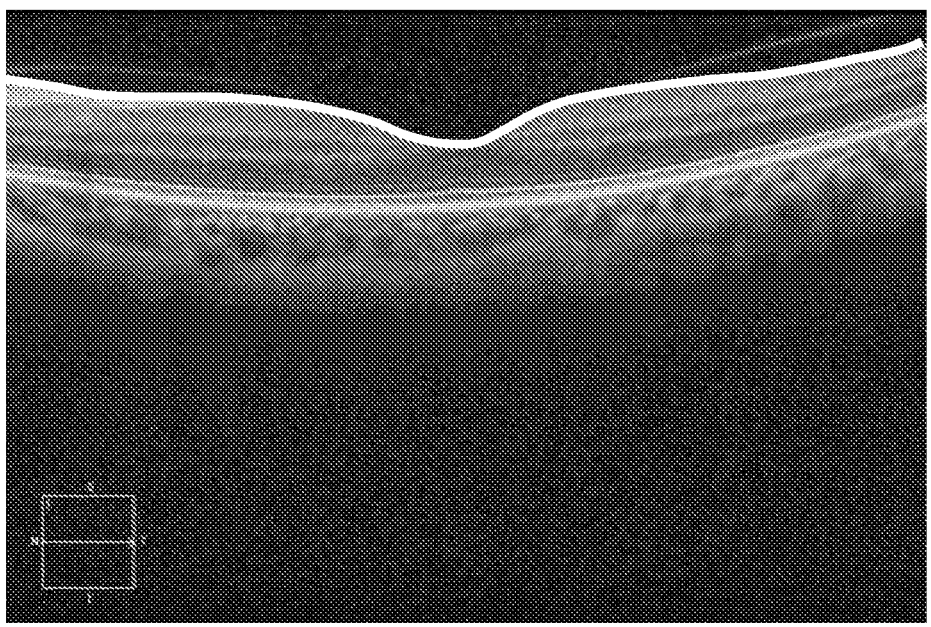
(d)
FIG. 13, continued

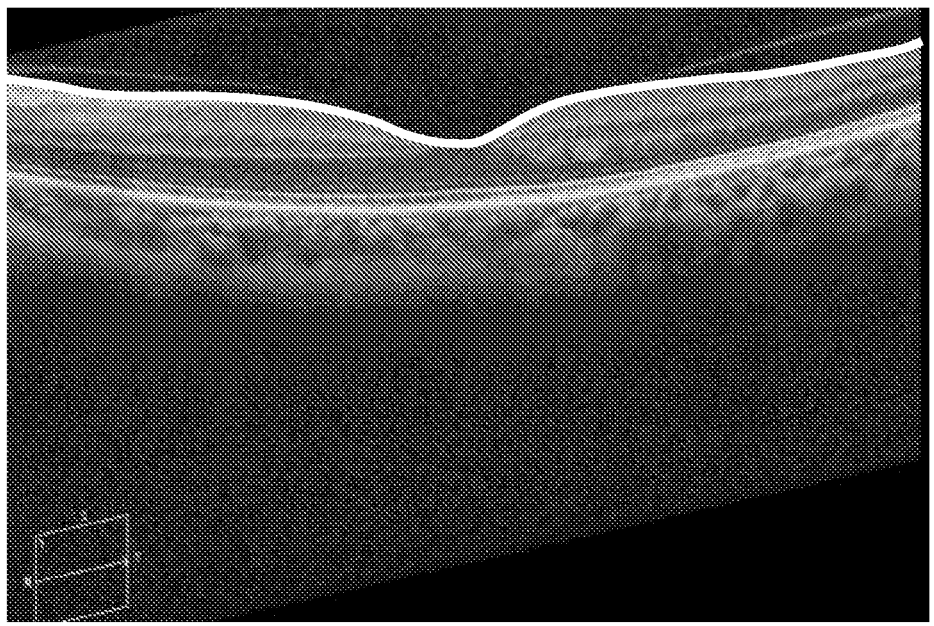
(e)
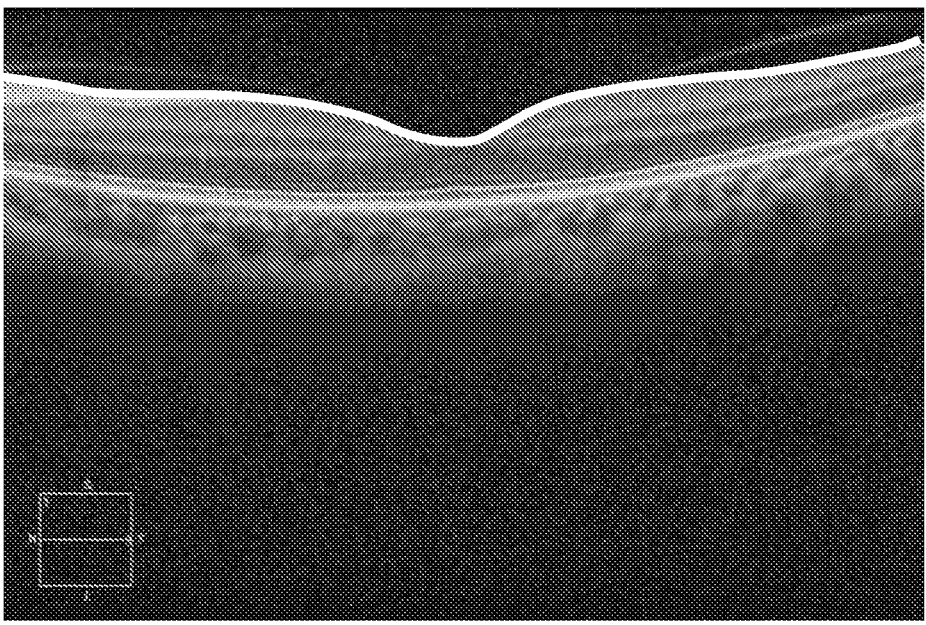
(f)
FIG. 13, continued (a)

(b)

(c)

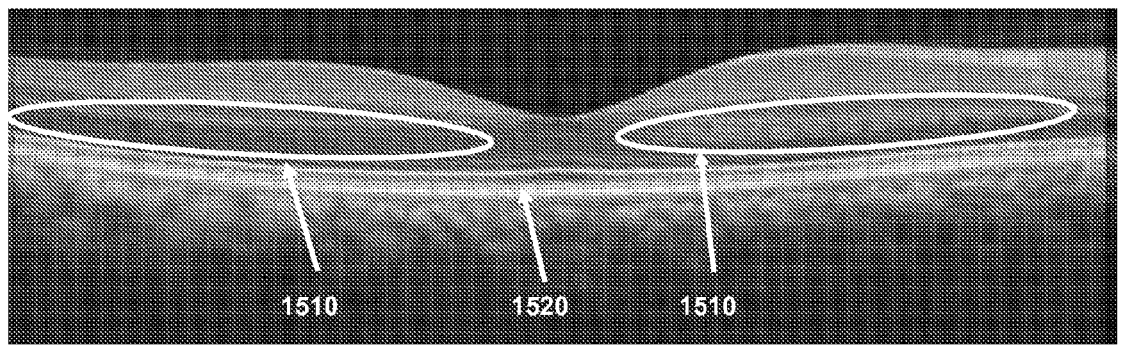
(d)
FIG. 15, continued (a)

(b)

(c)

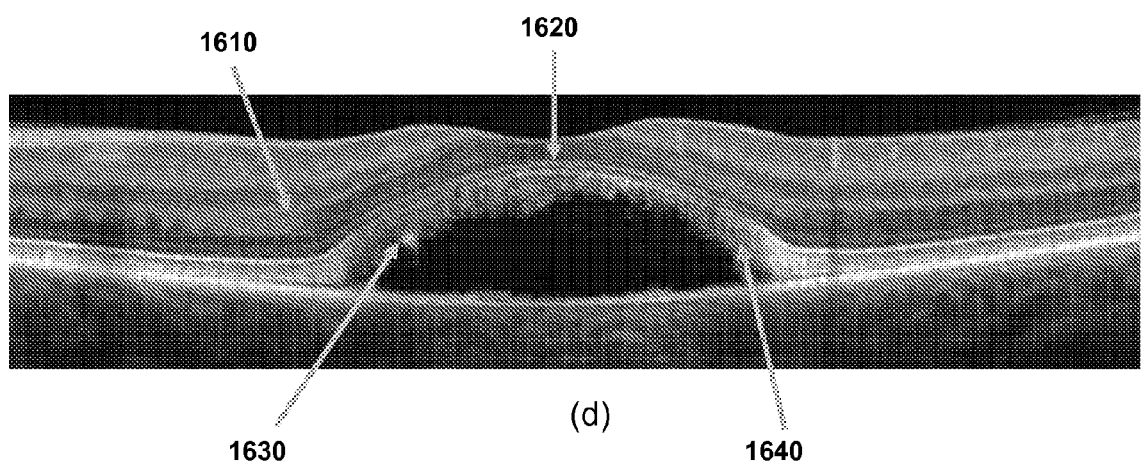
FIG. 16, continued

DIRECTIONAL OPTICAL COHERENCE TOMOGRAPHY SYSTEMS AND METHODS

CROSS-REFERENCE TO RELATED APPLICATIONS

Pursuant to 35 U.S.C. §119(e), this application claims priority to the filing date of U.S. Provisional Patent Application Ser. No. 61/600,495, filed Feb. 17, 2012, the disclosure of which is herein incorporated by reference.

REFERENCE TO GOVERNMENT SUPPORT

This invention was made with government support under grant numbers EY017269 and EY017607 awarded from the National Institutes of Health National Eye Institute. The government has certain rights in this invention.

INTRODUCTION

Optical coherence tomography (OCT) is an imaging technology able to produce images of the internal microstructure of a sample (e.g., living tissues). OCT is an interferometric technique based on low coherence interferometry, which utilizes a light source with low temporal coherence. In an OCT instrument, an optical interferometer is used to detect only coherent light. Light reflected by the sample interferes with light returning from a reference mirror. Coherent light is then detected and its depth profile measured. Subsequent beams are scanned across the sample and used to form an image.

SUMMARY

An optical coherence tomography system that includes an optical device having an adjustable optical element configured to displace a pupil entry point of light is provided. Optical coherence tomography methods using the optical coherence tomography system are also provided. The subject optical coherence tomography systems and methods find use in a variety of different applications, including imaging applications.

Embodiments of the present disclosure include an optical coherence tomography system. The system includes a light source, an objective lens configured to direct light from the light source along an optical axis, and an optical device. The optical device includes an adjustable optical element configured to displace a pupil entry point of the light, and a mechanism operatively coupled to the optical element and configured to rotate the optical element about one or more axes of rotation.

In some embodiments, the optical element is positioned between the light source and the objective lens. In some embodiments, the optical element is positioned such that light from the light source passes through the objective lens before contacting the optical element.

In some embodiments, the optical element includes an optically reflective element. In some embodiments, the optical element includes an optically transmissive element.

In some embodiments, the axis of rotation is normal to the optical axis.

In some embodiments, the system includes a scanner positioned between the light source and the objective lens and configured to scan the light from the light source in at least one dimension.

In some embodiments, the system includes a photodetector configured to detect light and generate data from the detected light.

In some embodiments, the system includes a processor configured to analyze the data to produce an image.

In some embodiments, the light source includes a spectrally tunable light source.

Embodiments of the present disclosure include an optical device for an optical coherence tomography system. The optical device includes an adjustable optical element configured to displace a pupil entry point of light, a mechanism operatively coupled to the optical element and configured to rotate the optical element about one or more axes of rotation, and an attachment element configured to attach the optical device to an optical coherence tomography system.

In some embodiments, the optical element includes an optically reflective element. In some embodiments, the optical element includes an optically transmissive element.

In some embodiments, the mechanism is configured to adjust the position of the optical element while the system displays an apparently unchanged internal fixation target to the subject.

Embodiments of the present disclosure includes an optical coherence tomography method that includes transmitting light from a light source towards a subject along an optical axis, where the light is transmitted through an optical device that includes an adjustable optical element configured to displace a pupil entry point of the light, and where the light contacts a sample area of the subject at an incident angle.

In some embodiments, the method includes adjusting the incident angle by rotating the optical element about one or more axes of rotation.

In some embodiments, the axis of rotation is normal to the optical axis.

In some embodiments, the light contacting the sample area of the subject illuminates a field of view on the sample area and the adjusting maintains substantially the same field of view.

In some embodiments, the adjusting includes positioning the optical element through a sequence of positions while displaying an apparently unchanged internal fixation target to the subject.

In some embodiments, the method includes detecting light reflected by the sample area using a photodetector configured to generate data corresponding to the detected light.

In some embodiments, the method includes transmitting the data to a processor for analysis.

In some embodiments, the method includes analyzing the data at one or more incident angles to produce an image of the sample area.

In some embodiments, the analyzing includes registration and normalization of the images.

In some embodiments, the analyzing includes comparing a first image produced at a first incident angle with one or more images produced at one or more corresponding incident angles to produce one or more composite images.

In some embodiments, the method includes color coding the composite image based on the contributions from different incident angles of the light.

In some embodiments, the image is a two-dimensional image. In some embodiments, the image is a three-dimensional image.

In some embodiments, the method includes spectrally enhancing image contrast to produce cross-sectional and volumetric segmentations and measurements of the sample area of the subject.

BRIEF DESCRIPTION OF THE FIGURES

FIGS. 11(d)-(f) show the same OCT images after registration and alignment. FIG. 11(g) shows a composite image of FIGS. 11(d)-(f).

FIGS. 13(c)-(f) show the same pair of OCT images during registration and alignment.

FIG. 15(d)) shows a composite image of FIGS. 15(a)-(c) after color coding.

FIG. 16(d) shows a composite image of FIGS. 16(a)-(c) after color coding.

DETAILED DESCRIPTION

Figure 1:
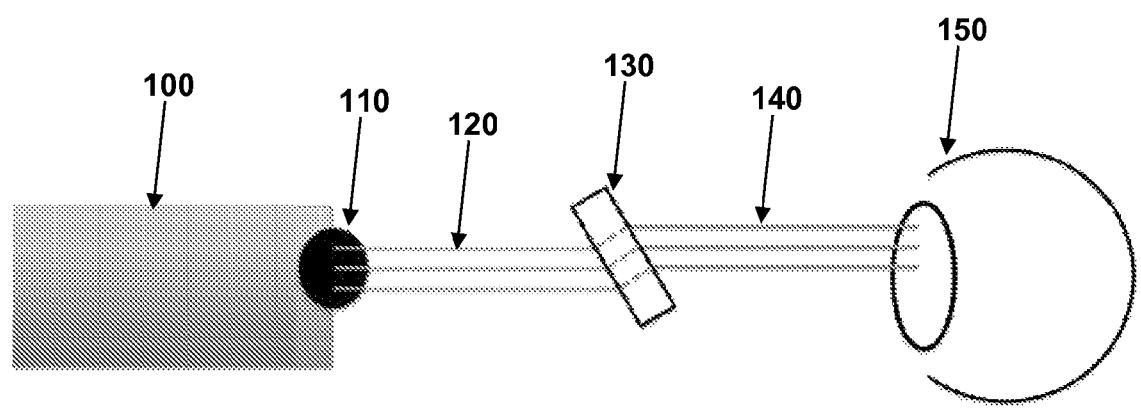
FIG. 1 shows a schematic of an optical coherence tomography (OCT) system that includes a rotatable optically transmissive element between the objective lens of the OCT system and the subject, according to embodiments of the present disclosure.

An optical coherence tomography system that includes an optical device having an adjustable optical element configured to displace a pupil entry point of light is provided. Optical coherence tomography methods using the optical coherence tomography system are also provided. The subject optical coherence tomography systems and methods find use in a variety of different applications, including imaging applications.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the present disclosure, embodiments of the optical coherence tomography systems and devices are described first in greater detail. Following this description, a description of optical coherence tomography methods using the subject optical coherence tomography systems and devices is provided. Finally, a review of the various applications in which the systems, devices and methods find use is provided.

Optical Coherence Tomography Systems

In certain embodiments, the subject directional optical coherence tomography (OCT) system includes a light source that generates light (e.g., an OCT beam). The system also includes an objective lens configured to direct light from the light source to along an optical axis. The light may be directed towards a sample area of a subject. In certain instances, the system includes an optical device configured to direct light from the light source to a sample area of a subject. In some cases, the optical device includes an adjustable optical element positioned in the path of the light. The adjustable optical element may be configured to direct light from the light source to the sample area while displacing the optical axis of the light. By "displacing" is meant that the optical axis of the light is moved from an initial position to a second position. For example, the optical axis of the light may be displaced in an x-direction or a y-direction or in a combination of both directions relative to the initial position of the optical axis. In certain cases, displacing the optical axis of the light may correspondingly displace the entry point of the light on the pupil of the subject (e.g., the pupil entry point). As such, the optical device may be configured to displace the optical axis of the light such that the pupil entry point of the light is different from the initial pupil entry point of the light. In certain embodiments, an OCT system that includes an optical device configured to displace the pupil entry point of the light from an initial pupil entry point may facilitate obtaining directional OCT images as described in more detail herein. In some instances, the optical device is configured to displace the pupil entry point of the light without substantially changing the position of the subject relative to the system. As such, in some cases, the relative positions of the subject and the system are not substantially changed as the directional OCT images are obtained.

In some embodiments, the adjustable optical element has substantially no effect on the OCT beam position. Stated another way, the adjustable optical element may be configured to not displace the optical axis of the OCT beam, and thus not displace the pupil entry point of the OCT beam. In other cases, when the adjustable optical element is re-positioned (e.g., rotated about one or more axes of rotation), the optical element may laterally displace the optical axis of the OCT beam, and thus may displace the pupil entry point. In certain cases, although the OCT beam may be laterally displaced by the adjustable optical element, the overall direction of the OCT beam is substantially maintained, which as described above causes the pupil entry point to shift. Thus, the system is configured to allow the OCT beam to be directed towards different pupil entry points. In some cases, multiple pupil entry points allow visualization of directionally reflective tissues which have clinical importance in health and disease. In certain embodiments, the system is configured to offset the pupil entry point form an initial position by 0.1 mm or more, such as 0.2 mm or more, including 0.3 mm or more, or 0.4 mm or more, or 0.5 mm or more, or 0.6 mm or more, or 0.7 mm or more, or 0.8 mm or more, or 0.9 m or more, or 1 mm or more, or 1.5 mm or more, or 2 mm or more, or 3 mm or more, or 4 mm or more, or 5 mm or more, or 7 mm or more, or 10 mm or more.

In certain instances, when the optical element is repositioned, the light may be displaced while maintaining the overall direction of the light, which causes the pupil entry point to shift while scanning the same retinal location. As such, the system may be configured to obtain one or more images of a retinal location at one or more corresponding pupil entry points. In certain embodiments, although the light is displaced from the initial position of the light, both beams of light may contact the retina at the same areas. In these embodiments, because the pupil entry point has been displaced, light contacts the retina at an incident angle different from that of the initial beam of light. In some instances, this allows imaging of the same area of the retina from different incident angles, depending on the position of the adjustable optical element.

In certain embodiments, the adjustable optical element is configured to rotate about one or more axes of rotation. For example, the optical element may be configured to rotate about one axis of rotation, such as a longitudinal axis. In other embodiments, the optical element is configured to rotate about its horizontal axis. In yet other embodiments, the optical element is configured to rotate about two or more axes of rotation, such that the optical element can be pivoted in any desired direction. In certain instances, the optical element is configured to pivot about a pivot point. The optical element may be pivoted in any desired direction about its pivot point to adjust the position of the optical element as desired.

As indicated above, the system includes an optical device that has an adjustable optical element positioned in the path of the light (e.g., OCT beam) as described above. In certain embodiments, the adjustable optical element is an optically transmissive element. In some cases, the optically transmissive element is configured to allow light to be transmitted through the optically transmissive element. For example, the optically transmissive element may have a transmittance of 75% or more, such as 80% or more, including 90% or more, or 95% or more, or 99% or more. In some instances, the optically transmissive element allows substantially all the light directed at the optically transmissive element to be transmitted through the optically transmissive element. For example, an optically transmissive element, such as glass (e.g., a plate of glass), may be positioned between the objective lens of the system and the subject's eye.

In certain embodiments, the adjustable optically transmissive element is configured to be rotated about one or more of its axes. For instance, the optically transmissive element may be configured to be rotated about one axis of rotation, such as its longitudinal axis. Other embodiments of the optically transmissive element may be rotated about a horizontal axis, or two or more axes of rotation such that the optically transmissive element may be pivoted about a pivot point. In certain embodiments, the optically transmissive element may be rotated such that light from the system contacts the surface of the optically transmissive element at an angle normal to the surface of the optically transmissive element. For example, the optically transmissive element may be positioned such that the front and back surfaces of the optically transmissive element are substantially normal to the optical axis of the light (e.g., the beam of light projected from the objective lens of the system).

The optically transmissive element may also be positioned (e.g., rotated about one or more axes of rotation) such that light from the system contacts the surface of the optically transmissive element at a non-normal angle. For example, the optically transmissive element may be positioned such that the angle between the light from the system and the surface of the optically transmissive element is 90°, less than 90° or greater than 90°. The optically transmissive element may be positioned such that the angle between the light from the system and the surface of the optically transmissive element is at any arbitrary angle including or between 180° and 0°. For instance, the optically transmissive element may be positioned such that the angle between the light from the system and the surface of the optically transmissive element is 85° or less, including 80° or less, or 75° or less, or 70° or less, or 65° or less, or 60° or less, or 55° or less, or 50° or less, or 45° or less, or 40° or less, or 35° or less, or 30° or less, or 25° or less, or 20° or less, or 15° or less, or 10° or less, or 5° or less, or any angle including or between these angles or any fraction of an angle thereof. In some cases, the optically transmissive element may be positioned such that the angle between the light from the system and the surface of the optically transmissive element is 95° or more, including 100° or more, or 105° or more, or 110° or more, or 115° or more, or 120° or more, or 125° or more, or 130° or more, or 135° or more, or 140° or more, or 145° or more, or 150° or more, or 155° or more, or 160° or more, or 165° or more, or 170° or more, or 175° or more, or any angle including or between these angles or any fraction of an angle thereof.

In some embodiments, the optical element has substantially no effect on the OCT beam position as described above. For example, the optically transmissive element may be oriented normal to the optical axis of the light. In these cases, when the optically transmissive element is oriented normal to the optical axis of the light, the optically transmissive element may cause substantially no lateral displacement of the light as the light passes through the optically transmissive element. In other cases, when the optically transmissive element is repositioned (e.g., rotated about one or more axes of rotation), the optically transmissive element may laterally displace the OCT beam, and thus may displace the optical axis of the OCT beam and the pupil entry point. In certain cases, although the OCT beam may be laterally displaced by the optically transmissive element, the overall direction of the OCT beam is substantially maintained, which as described above causes the pupil entry position to shift.

As indicated above, the system includes an optical device that has an adjustable optical element positioned in the path of the light (e.g., OCT beam) as described above. In certain embodiments, the optical element is an optically reflective element. In some cases, the optically reflective element is configured to reflect light directed at the surface of the optically reflective element. For example, the optically reflective element may have a reflectance of 75% or more, such as 80% or more, including 90% or more, or 95% or more, or 99% or more. In some instances, the optically reflective element reflects substantially all the light directed at the optically reflective element. For example, the optically reflective element may be a mirror, such as a rotatable mirror, a pivotable mirror, a deformable mirror, or an adaptive optics mirror.

In certain embodiments, the optically reflective element is configured to be rotated about one or more of its axes of rotation. For instance, the optically reflective element may be configured to be rotated about one axis of rotation, such as its longitudinal axis, with respect to the incident light from the light source. Other embodiments of the optically reflective element may be rotated about a horizontal axis, or two or more axes of rotation such that the optically reflective element may be pivoted about a pivot point. In certain embodiments, the optically reflective element may be positioned such that light from the light source of the system is reflected towards a subject, such as a sample area of a subject (e.g., the eye or pupil). The optically reflective element may also be configured to rotate about one or more of its axes to laterally displace the reflected light. For example, the optically reflective element may be rotated (or pivoted) from its initial position by an angle of 0.1° or more, including 0.3° or more, or 0.5° or more, or 1° or more, or 1.5° or more, or 2° or more, or 2.5° or more, or 3° or more, or 3.5° or more, or 4° or more, or 4.5° or more, or 5° or more, or any angle including or between these angles or any fraction of an angle thereof. In certain embodiments, small changes on the positioning of the optically reflective element may be used to laterally displace the reflected light. For example, the optically reflective element may be rotated (or pivoted) from its initial position by an angle of 1° or less, such as 0.5° or less, including 0.1° or less, or 0.05° or less, or 0.01° or less, or 0.005° or less, or 0.001° or less, or any angle including or between these angles or any fraction of an angle thereof.

In some embodiments, the optically reflective element is configured to reflect light from the light source of the system towards the subject such that the light has an initial optical axis and thus an initial pupil entry point. In some cases, when the optically reflective element is rotated about one or more of its axes (e.g., its longitudinal axis), the optically reflective element may laterally displace the light reflected from the optically reflective element, and thus may displace the optical axis of the OCT beam and the pupil entry point. In certain cases, although the OCT beam may be laterally displaced by the optically reflective element, the overall direction of the OCT beam is substantially maintained, which as described above causes the pupil entry position to shift.

In some instances, the optical device is such that light from the light source passed through the objective lens before contacting the adjustable optical element. Stated another way, the optical device may be positioned between the objective lens and the subject. As used herein, a lens is an optical device that is configured to transmit and refract light, converging or diverging the beam of light as the light passes through the lens. In other instances, the optical device is positioned between the light source and the objective lens. One or more additional lenses may be included in the system as desired. The objective lens may be any type of lens conventionally used in an OCT system. In certain instances, the objective lens is configured to direct light from the light source towards a subject along an optical axis (e.g., the optical axis of the objective lens). In some embodiments, the objective lens is the lens of the system positioned nearest to the subject. For instance, the objective lens may be the final lens the light from the system passes through before contacting the subject. As described in more detail below, in some cases, the optically transmissive element is not a lens.

The light source may be any type of light source conventionally used in an OCT system, such as, but not limited to an infrared light source, a visible light source, and the like. In certain embodiments, the light source is a broadband light source configured to emit light over a broad range of frequencies. For example, the light source may include an LED (e.g., a superluminescent diode), a laser (e.g., a femtosecond laser), etc. The light source may have an optical axis, which is an axis that defines the path along which light propagates through the system. For instance, light from the light source may be transmitted through the objective lens along an optical axis.

Aspects of the system may further include a scanner. The scanner may be configured to scan the light from the light source in at least one dimension. In some instances, the scanner is configured to scan the light form the light source in one dimension. In other instances, the scanner is configured to scan light from the light source in two dimensions (e.g., in an x-direction and a y-direction). By scanning the light from the light source, the scanner displaces the beam of light from the OCT system such that different areas of the subject can be imaged, for example different areas of the retina. In some cases, the scanner is positioned between the light source and the objective lens of the system. In certain cases, the scanner includes a mirror and a rotation mechanism configured to rotate the mirror. Light from the light source may be reflected off the mirror at a certain angle and by rotating the mirror, the angle of reflection may be changed such that the reflected light is scanned across the sample area of the subject. In some cases, the rotation mechanism of the scanner includes a galvanometer. In certain embodiments, the scanner is configured such that light from the light source is scanned across the sample area while the pupil entry point is not substantially changed from its initial position. For example, the scanner may be configured to scan light from the light source in one dimension or in two dimensions while maintaining the same pupil entry point.

In certain embodiments, the OCT system includes a photodetector. The photodetector may be configured detect light reflected from the sample area of the subject (e.g., the retina). In some cases, the photodetector is configured to detect light reflected from the subject, but not light scattered by the subject. The photodetector can be any type of photodetector that finds use in an OCT system, such as, but not limited to, a charge-coupled device (CCD) sensor, an intensified charge-coupled device (ICCD), a complementary metal oxide semiconductor (CMOS) sensor, and the like. The photodetector may be configured to generate data (e.g., image data) from the detected light.

In certain instances, the OCT system includes a processor. The processor may be operatively coupled to the photodetector, such that the data generated by the photodetector is transmitted to the processor for further analysis. In some cases, the processor is configured to analyze the data from the photodetector to produce an image. In certain instances, the processor is included in the OCT system. For example, image data may be acquired and analyzed by a processor integrated into the OCT system. In other instances, the processor is located remotely from the OCT system. In these embodiments, the OCT system may be configured to transmit the data from the OCT system to the processor, such as through a wired connection or wirelessly. In other embodiments, pre-processing of the raw image data may be performed by a first processor integrated into the OCT system, and further processing (e.g., registration, normalization and image rendering as described herein) may be performed by a second processor. The processor, whether included in the OCT system or located remotely from the OCT system may be included in a computer programmed to analyze the data from the photodetector to produce an image. Additional aspects of a processor programmed for operation in an OCT system are found in U.S. Pat. Nos. 7,145,661, 7,835,010; U.S. Application Publication Nos. 2010/0265511, 2011/0101207; and Lujan, B. J., et al. *Investigative Ophthalmology & Visual Science,* 2011, vol. 52, no. 3, the disclosures of each of which are incorporated herein by reference.

Additional aspects of the system include one or more other elements that facilitate operation of the system by a user, such as, but not limited to, a user input device (e.g., a keyboard, one or more buttons, a mouse, a touchscreen, etc.), an output device, such as a display or a printer, and the like.

FIG. 1 shows a schematic of an optical coherence tomography (OCT) system that includes a rotatable optically transmissive element between the objective lens of the system and the subject. The system 100 includes an objective lens 110. Light 120 from a light source in the system 100 passes through the objective lens 110 and contacts an optically transmissive element 130. As shown in FIG. 1, the optically transmissive element 130 is rotated such that it is at a non-normal (e.g., not 90°) angle relative to the optical axis of the light transmitted through the objective lens 110. The light that is transmitted through the optically transmissive element 130 is displaced relative to the initial optical axis of the light transmitted through the objective lens 110. The displaced light 140 then contacts the subject (e.g., the eye 150) at a pupil entry point that is offset from the position the light would have contacted the subject had the optically transmissive element 130 been oriented normal to the optical axis of the light transmitted through the objective lens 110. Other rotational positions for the optically transmissive element are possible, depending on the desired OCT beam offset. For example, the optically transmissive element may have a rotational position such that the optically transmissive element is normal to the optical axis of the OCT beam. In these instances, where the optically transmissive element is normal to the optical axis of the OCT beam, the optically transmissive element may not substantially displace the optical axis of the OCT beam, and thus may not substantially displace the pupil entry point.

Figure 2:
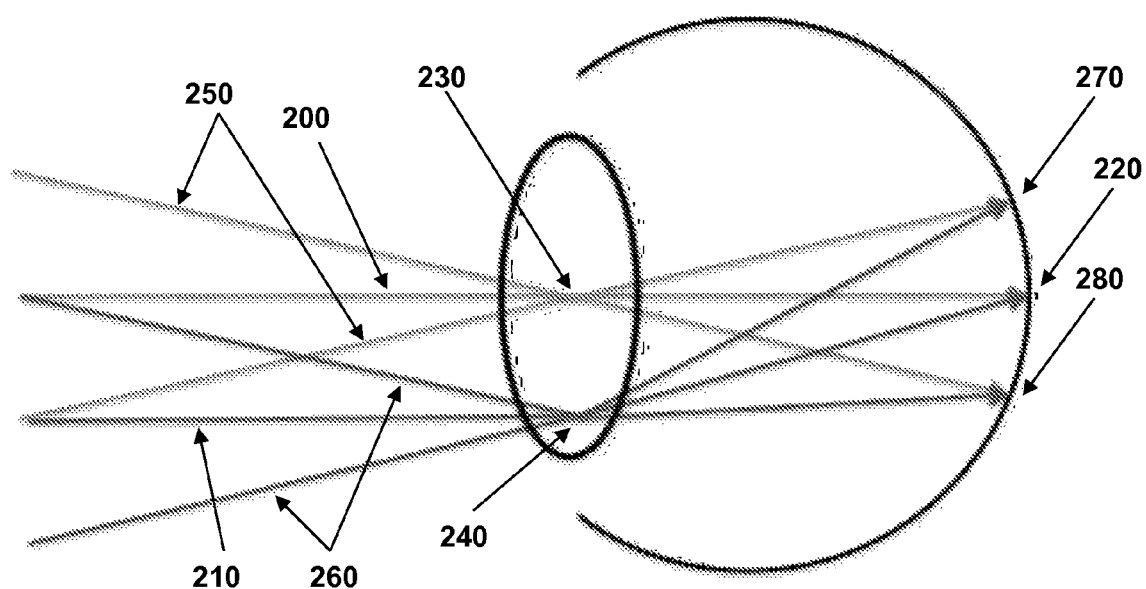
FIG. 2 shows a schematic of imaging the same parts of a subject's retina by a scanning beam with a pivot point in the pupil plane at two different pupil entry positions resulting in different angles of incidence of light on the retina, according to embodiments of the present disclosure.

FIG. 2 shows a schematic of imaging the same areas of a subject's retina at two different incident angles. As shown in FIG. 2, light 200 contacts a subject's retina at a first incident angle. The adjustable optical element (not shown) is positioned at an initial position such that the light has an initial pupil entry point 230 in the pupil plane. Also shown in FIG. 2 is light 210, which has been displaced relative to the optical axis of the light transmitted through the objective lens due to the optical element being repositioned (e.g., rotated or pivoted) to a second position. The displaced light 210 is offset from light 200 and thus contacts the eye at a second pupil entry point 240 in the pupil plane, which is offset from the initial pupil entry point 230 where light contacts the eye. As shown in FIG. 2, although light 210 is offset from light 200, both beams of light contact the retina at the same area 220. Light 210 contacts the retina at an incident angle different from that of light 200. In some cases, this facilitates imaging of the same area of the retina from different incident angles, depending on the rotational position of the rotatable optical element. Light 200 may be scanned using a scanning mirror to direct the light 250 through the same pupil entry point 230 to image adjacent areas of the retina 270 and 280. Similarly, light 210 may be scanned using a scanning mirror to direct the light 260 through the same pupil entry point 240 to image adjacent areas of the retina 270 and 280. Light 260 contacts the retina at different incident angles from that of light 250.

Figure 3:
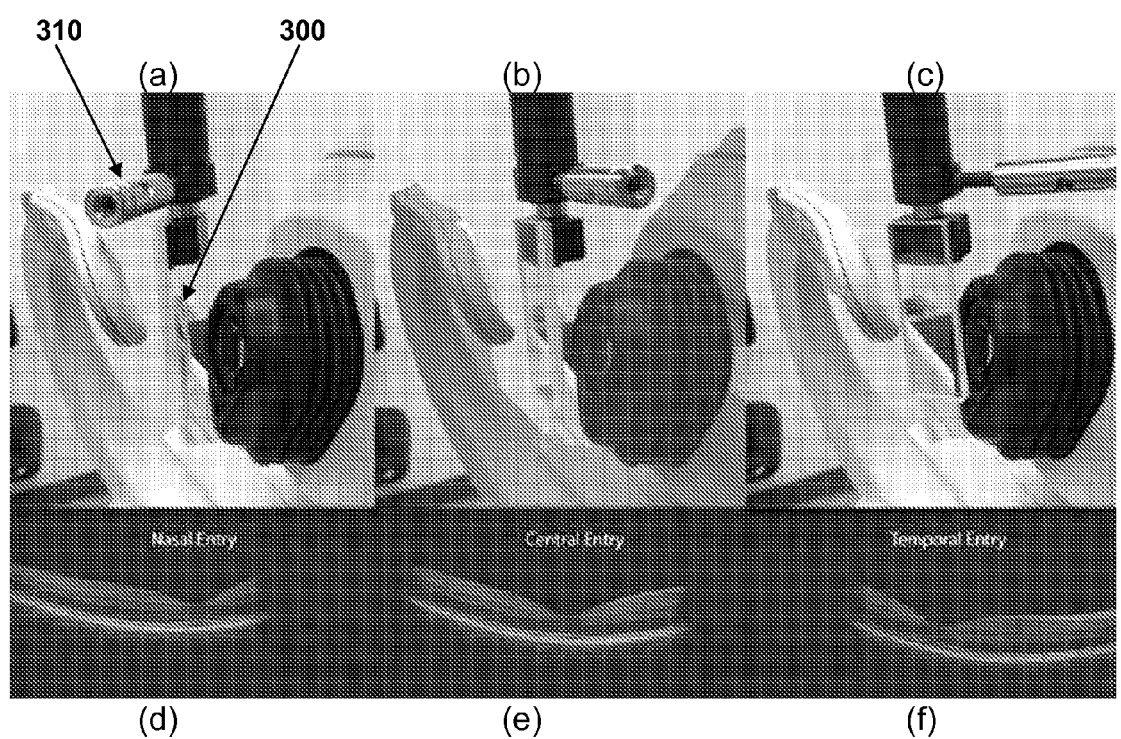
FIG. 3 shows photographs of an OCT system with the rotatable optically transmissive element at three different positions (FIGS. 3(a)-3(c)), and the corresponding OCT images obtained at the three different positions (FIGS. 3(d)-3(f)), according to embodiments of the present disclosure.

FIG. 3 shows photographs of an OCT system with a rotatable optically transmissive element. The rotatable optically transmissive element is shown at three different positions (FIGS. 3(a)-3(c)). The corresponding OCT images of the same retinal location obtained from these three different positions is shown in FIGS. 3(d)-3(f). As shown in FIGS. 3(a)-3(c), the optically transmissive element 300 can be rotated by adjusting the position of handle 310.

Figure 4:
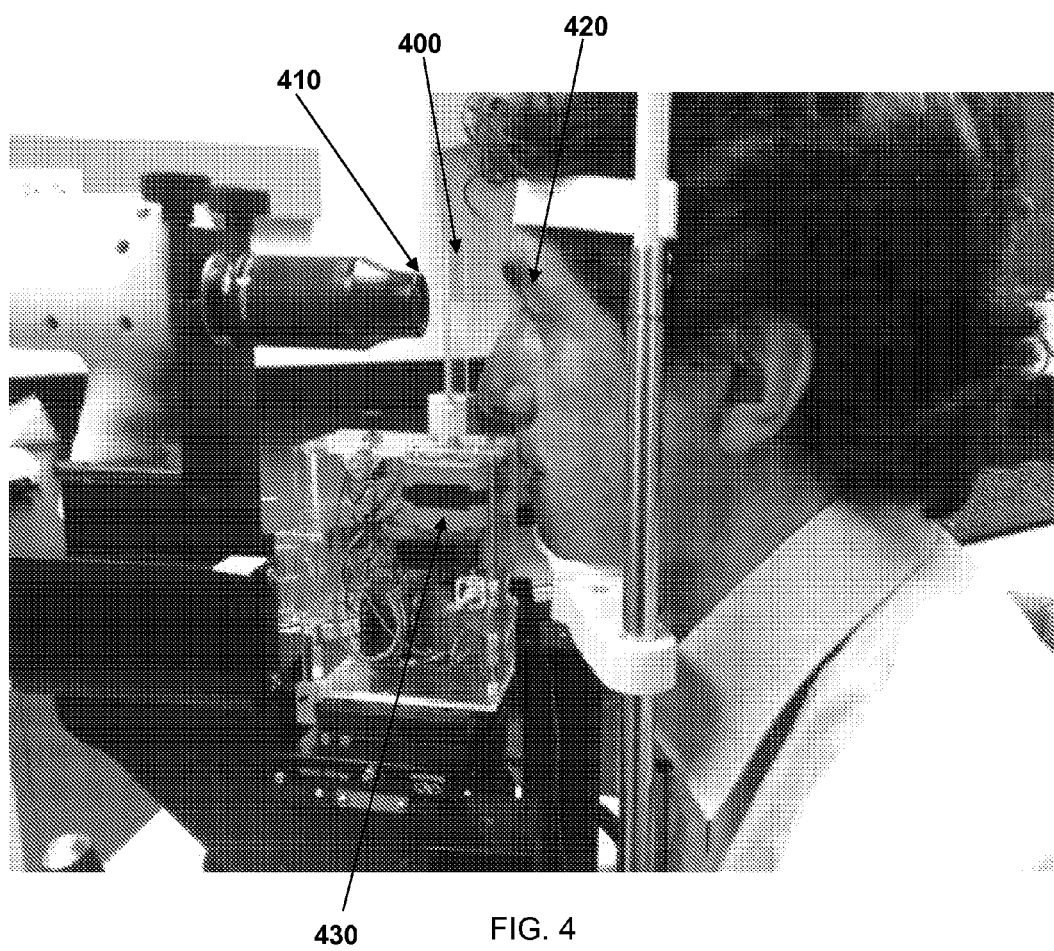
FIG. 4 shows a photograph of an OCT system of FIG. 1 in use, according to embodiments of the present disclosure.

FIG. 4 shows a photograph of an OCT system in use. In FIG. 4, the optically transmissive element 400 is positioned between the objective lens 410 of the OCT system and the subject 420. An adjustment mechanism 430 is operatively coupled to the optically transmissive element 400 and is configured to rotate the optically transmissive element. In some embodiments, the adjustment mechanism 430 is configured to rapidly adjust the sequence of rotational positions of the optically transmissive element 400 while the patient maintains fixation.

Figure 7:
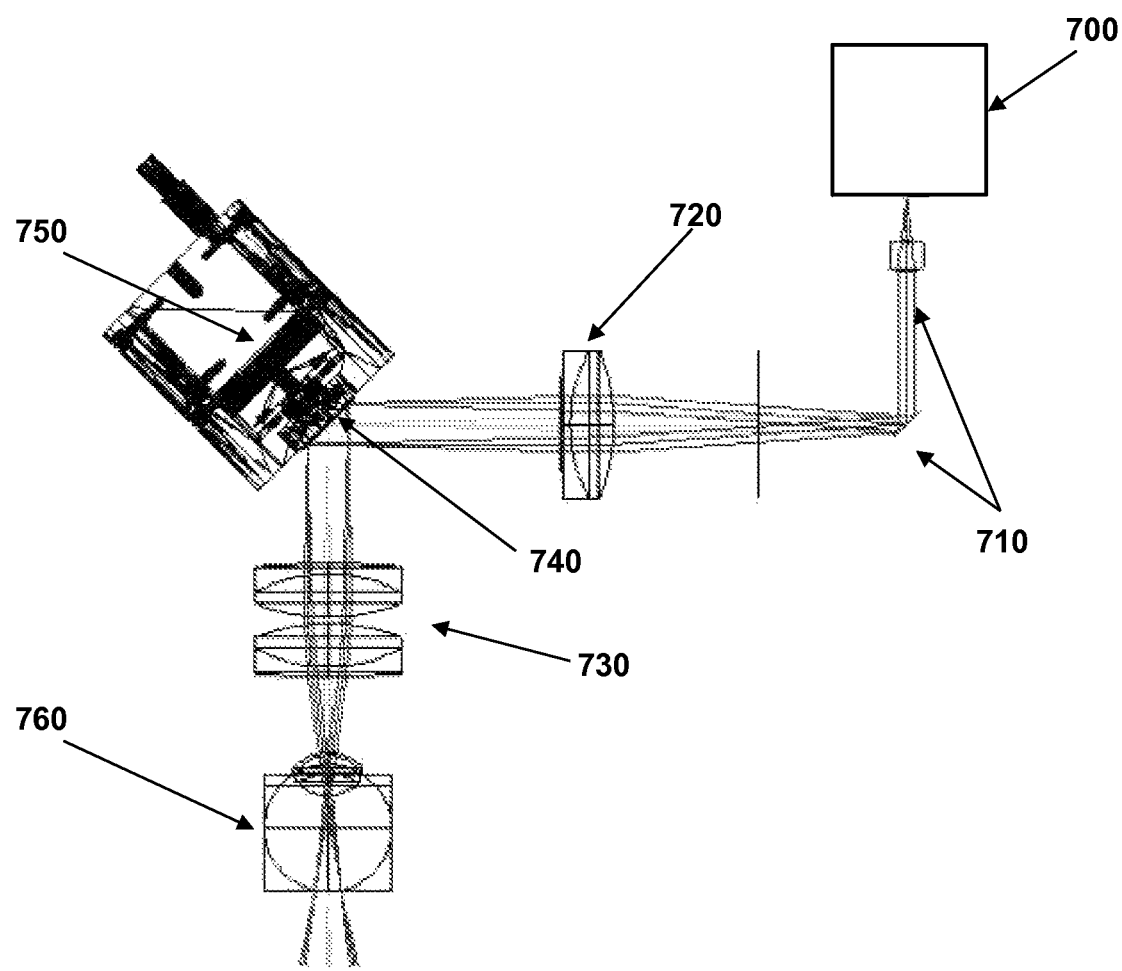
FIG. 7 shows a schematic of an OCT system that includes an optically reflective element mounted an a multi-axis rotatable stage between the light source and the objective lens, according to embodiments of the present disclosure.

FIG. 7 shows a schematic of an optical coherence tomography (OCT) system that includes a rotatable optically reflective element between the light source and the objective lens of the system. The system includes a light source 700 and an objective lens 730. The objective lens may include one or more lenses. For instance, as shown in FIG. 7, the objective lens 730 includes two lenses. Light from the light source 700 in the system is reflected by scanning mirrors 710 and then passes through a first lens 720. The light then contacts an optical device that includes an optically reflective element 740 which is located at the primary focal point of the first lens 720. The optically reflective element 740 is operatively coupled to an adjustment mechanism 750 that is configured to pivot the optically reflective element 740. The light that is reflected by the optically reflective element 740 passes through the objective lens 730, having its secondary focal point at 740, along an initial optical axis towards the subject 760. In some instances, a mirror may be positioned between the objective lens and the subject, depending on the configuration of the system. The light then contacts the subject (e.g., the eye) at an initial pupil entry point. Rotation of the optically reflective element 740 causes the light to be displaced relative to the initial optical axis. The displaced light then contacts the subject (e.g., the eye) at a pupil entry point that is offset from the initial pupil entry point.

Figure 8:
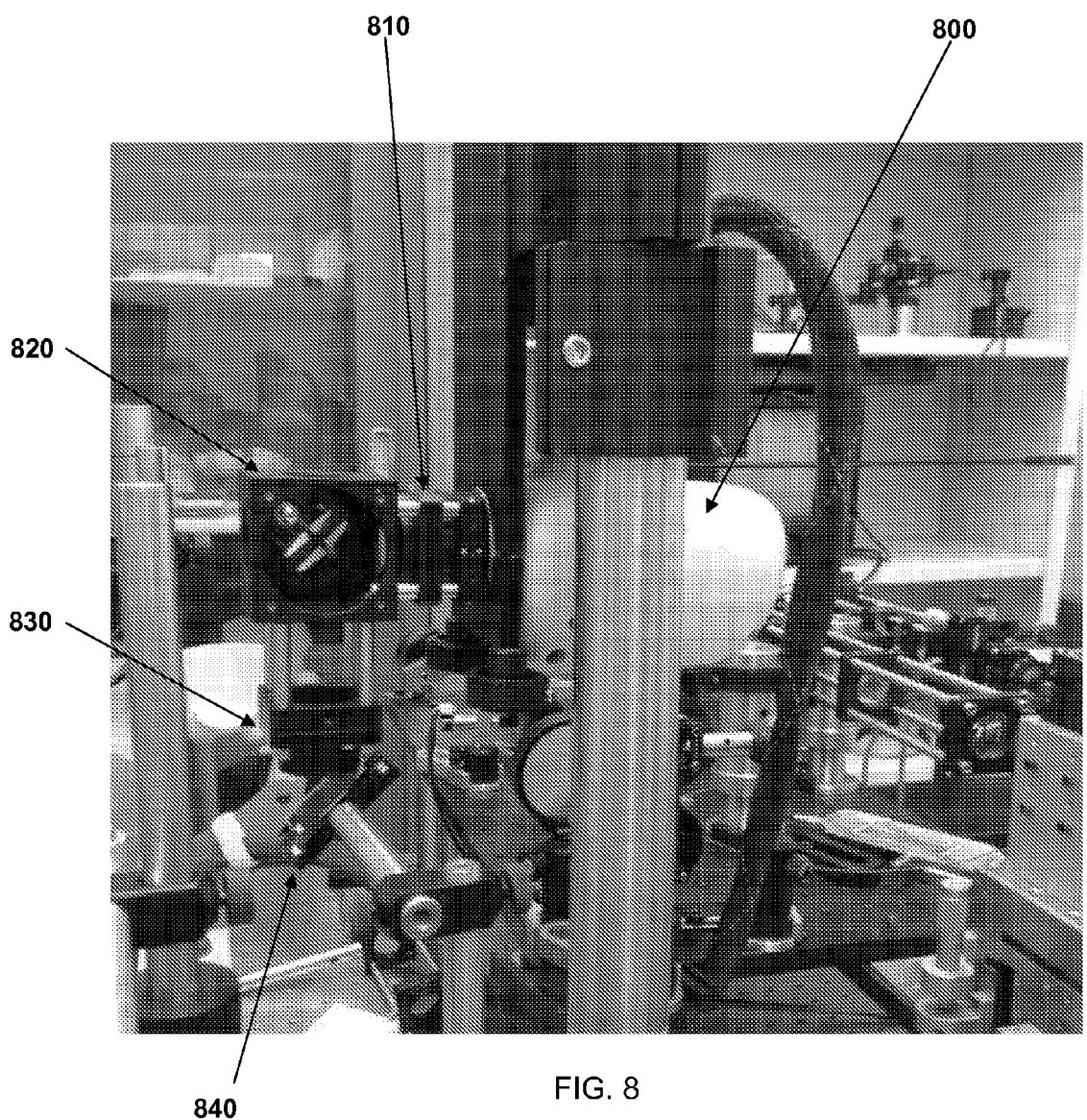
FIG. 8 shows a photograph of an OCT system of FIG. 7, according to embodiments of the present disclosure.

FIG. 8 shows a photograph of an OCT system that includes an optically reflective element. In FIG. 8, an optical device 820 that includes an optically reflective element is positioned between the light source 800 and the objective lens 830 of the OCT system. A motor is operatively coupled to the optically reflective element and is configured to rotate the optically reflective element. Also shown are the first lens 810 and dichroic mirror 840, allowing for an internal fixation target.

Optical Devices

As described above, an optical coherence tomography (OCT) system according to the present disclosure includes an optical device. The optical device for the OCT system includes an adjustable optical element and a mechanism configured to rotate the optical element about one or more axes of rotation. In some cases, the optical device includes an attachment element configured to attach the optical device to the OCT system.

As described above, in certain embodiments, the optical element is an optically transmissive element configured to allow light to be transmitted through the optically transmissive element. The optically transmissive element can be made of any convenient optically transmissive material, such as, but not limited to, glass (e.g., crown glass), plastic (e.g., polycarbonate), and the like. For example, the optically transmissive element can be made of crown glass, or glass with a higher refractive index (e.g., a refractive index of 1.5 or more). In some cases, the optically transmissive element is a glass plate. The optically transmissive element may have a front surface and a back surface, the front and back surfaces being the surfaces of the optically transmissive element through which the light from the OCT system passes. In some instances, the front surface and the back surface of the optically transmissive element are substantially parallel to each other. In certain embodiments, the optically transmissive element is not a lens or a prism.

In certain embodiments, the optically transmissive element is rectangular in shape. In some cases, the optically transmissive element has a thickness of 10 mm or less, such as 5 mm or less, or 3 mm or less, or 1 mm or less. In some instances, the optically transmissive element has a width of 75 mm or less, including 50 mm or less, or 25 mm or less. In some cases, the optically transmissive element has a height of 150 mm or less, such as 125 mm or less, including 100 mm or less, or 75 mm or less.

As described above, in certain embodiments, the adjustable optical element is an optically reflective element configured to reflect light. The optically reflective element may be made of any convenient reflective material. For example, the optically reflective element may include a substrate with a layer of a reflective material disposed on the surface of the substrate, such as a layer of a metal (e.g., gold).

In certain embodiments, the optical device includes a mechanism configured to adjust the position of the adjustable optical element. In certain instances, the mechanism may be configured to rotate the optical element about one or more axes of rotation. For example, the mechanism may be operatively coupled to the adjustable optical element and configured to rotate the optical element about one or more axes of rotation. In some cases, the axis of rotation is parallel to the longitudinal axis of the optical element (e.g., for a rectangular optical element). In other embodiments, the axis of rotation may be parallel to the horizontal axis of the optical element. In other embodiments, the axis of rotation is coplanar with the surface of the optical element and intersects a pivot point, such that the optical element may be pivoted about the pivot point as desired. As described above, the light from the light source of the system may be transmitted through the objective lens along an optical axis. In some cases, the axis of rotation is normal to the optical axis of the light.

For example, in systems that include an optically transmissive element, the mechanism may be configured to position the optically transmissive element such that the front and back surfaces of the optically transmissive element are substantially normal to the optical axis of the light (e.g., the beam of light projected from the objective lens of the system). For example, the angle between the optical axis of the light and the surface of the optically transmissive element may be 90°. In these cases, the light from the system may be transmitted through the optically transmissive element with substantially no displacement in the path of the light from the OCT system. In addition, the mechanism may be configured to position the optically transmissive element such that the light from the system contacts the surface of the optically transmissive element at a non-normal angle. For example, the mechanism may be configured to allow the optically transmissive element to be positioned such that the angle between the light from the OCT system and the surface of the optically transmissive element is less than 90° or greater than 90°, as described above.

In other embodiments, where the system includes an optically reflective element, the mechanism may be configured to position the optically reflective element at an initial position. In addition, the mechanism may be configured to position the optically reflective element at a second position such that the surface of the optically reflective element is at an angle with respect to the initial position of the optically reflective element, as described above.

In certain embodiments, as described above, the mechanism is an adjustment mechanism operatively coupled to the adjustable optical element and configured to adjust the position of the optical element. In some instances, the adjustment mechanism includes a motor. The motor may be configured to position the adjustable optical element as described above. Other types of mechanisms may be used, such as, but not limited to, a handle (e.g., a handle configured for manual adjustment of the optical element), a galvanometer, an actuator, a deformable mirror, an adaptive optics mirror, combinations thereof, and the like. In embodiments where the mechanism includes a motor or an actuator or the like, the mechanism may be operatively coupled to a processor, such as a processor as described above. In some cases, the processor is configured to control the position of the optical element by controlling the position of the mechanism that is operatively coupled to the adjustable optical element.

In some instances, the mechanism is configured to position the adjustable optical element from an initial position to a second position in a minimum amount of time. In some instances, rapid positioning of the optical element minimizes changes in patient fixation as the pupil entry point of the light is displaced. In certain embodiments, maintaining patient fixation on an internal fixation target may facilitate obtaining images from the same retinal area as the pupil entry point of the light is displaced. As such, the mechanism may be configured to adjust the position of the optical element while the system displays an apparently unchanged internal fixation target to the subject.

In certain embodiments, the optical device includes an attachment element configured to attach the optical device to the system. For example, the attachment element may include one or more fasteners, such as, but not limited to a screw, a bolt, a clip, a clamp, a magnet, combinations thereof, and the like. The attachment element may be configured to securely attach the optical device to the system, such that there is substantially no relative movement between the optical device and the system during use. In these embodiments, securely attaching the optical device to the system may facilitate an accurate determination of the angle between the optical axis of the light from the system and the rotatable optical element of the optical device.

Methods

Aspects of the present disclosure include optical coherence tomography methods. In certain embodiments, the method includes transmitting light from a light source towards a sample along an optical axis. The light is transmitted through an optical device that includes a rotatable optical element configured to displace a pupil entry point of the light as described above. The light contacts the sample at an incident angle. By "incident angle" is meant the angle between a beam of light contacting a surface and a line perpendicular to the surface at the point of contact.

In certain embodiments, the method includes displacing the pupil entry point of the light using the adjustable optical element. As described above, the incident angle of the light on the sample area (e.g., retina) may depend on the position of the adjustable optical element. As such, the method may include adjusting the incident angle by repositioning the optical element. As discussed above, the optical element can be rotated about an axis of rotation or pivoted about a pivot point. In some cases, the axis of rotation is normal to the optical axis of the light from the system. As such, the method may include rotating the optical element about an axis of rotation normal to the optical axis of the light.

In certain embodiments, the light contacting the sample illuminates a field of view on the sample. The field of view corresponds to the sample area of the subject that can be imaged by the light. In certain instances, adjusting the incident angle by repositioning the optical element does not substantially change the field of view, such that substantially the same field of view is maintained at different incident angles. Maintaining substantially the same field of view while repositioning the optical element may facilitate imaging the same areas of the subject from different incident angles. In some cases, imaging the same area of the subject from different incident angles may facilitate the generation of high contrast images of that sample area of the subject.

Aspects of the method may further include detecting the light reflected by the sample using a photodetector. As discussed above, the photodetector may be configured to generate data (e.g., image data) corresponding to the detected light. The method may include detecting reflected light from the sample. In some embodiments, light scattered by the sample away from the detector is not substantially detected.

In certain embodiments, the method includes transmitting the image data to a processor for analysis. The processor may be included in the system, or may be included in an external processing device (e.g., a computer). In some cases, the method includes analyzing the data at one or more incident angles to produce an image of the sample. In certain cases, the image produced is a two dimensional (e.g., cross-sectional) image. In other cases, the image produced is a three-dimensional (e.g., volumetric) image.

In some instances, the incident angle is 0° (e.g., the light is normal to the surface of the sample). In certain instances, the incident angle is greater than 0°, as measured from a line normal to the surface of the sample. For example, the incident angle can be any angle (or fraction thereof) between 0° and 90°, such as 5°, 10°, 15°, 20°, 25°, 30°, 35°, 40°, 45°, 50°, 55°, 60°, 65°, 70°, 75°, 80°, 85°, etc. In certain embodiments, multiple images may be obtained at various different incident angles over a period of time. For example, the apparent angle of the retina, which is proportional to the incident angle, may range from ±25°, such as ±20°, or ±15°, including ±10°, or ±5°, or ±1°. Multiple images may be obtained at various different angles over a period of time, such as 1 min or less, or 45 seconds or less, or 30 seconds or less, or 15 seconds or less, or 10 seconds or less, or 5 seconds or less, or 4 seconds or less, or 3 seconds or less, or 2 seconds or less, or 1 second or less.

Figure 9:
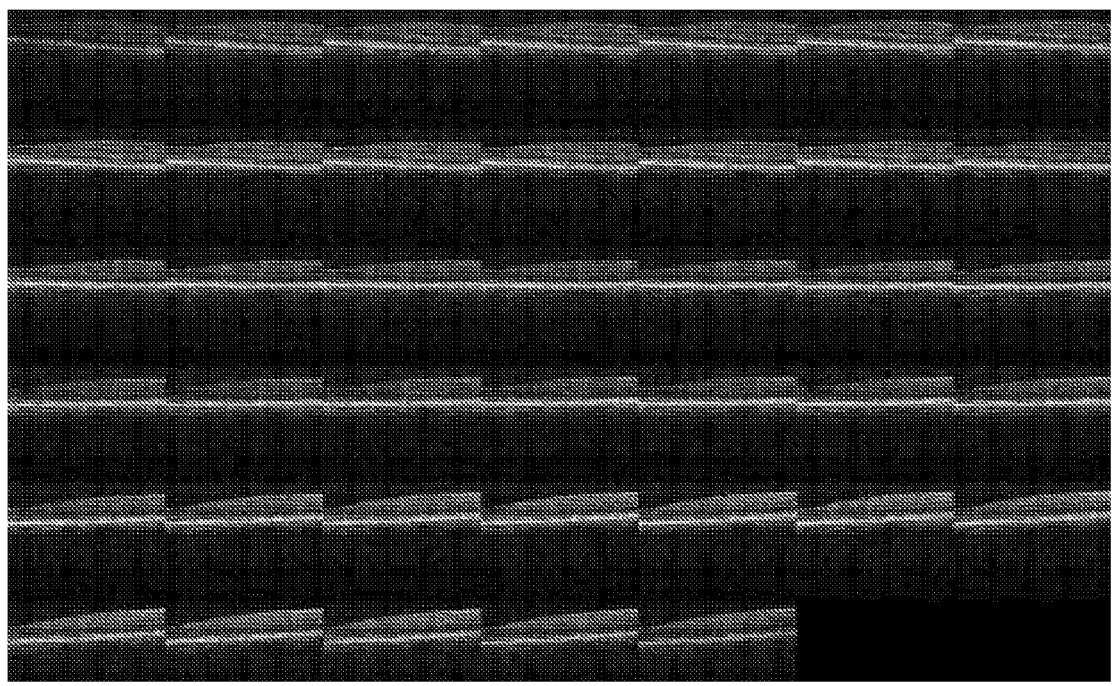
FIG. 9 shows a series of OCT images obtained over time at various different incident angles, according to embodiments of the present disclosure.
Figure 10:
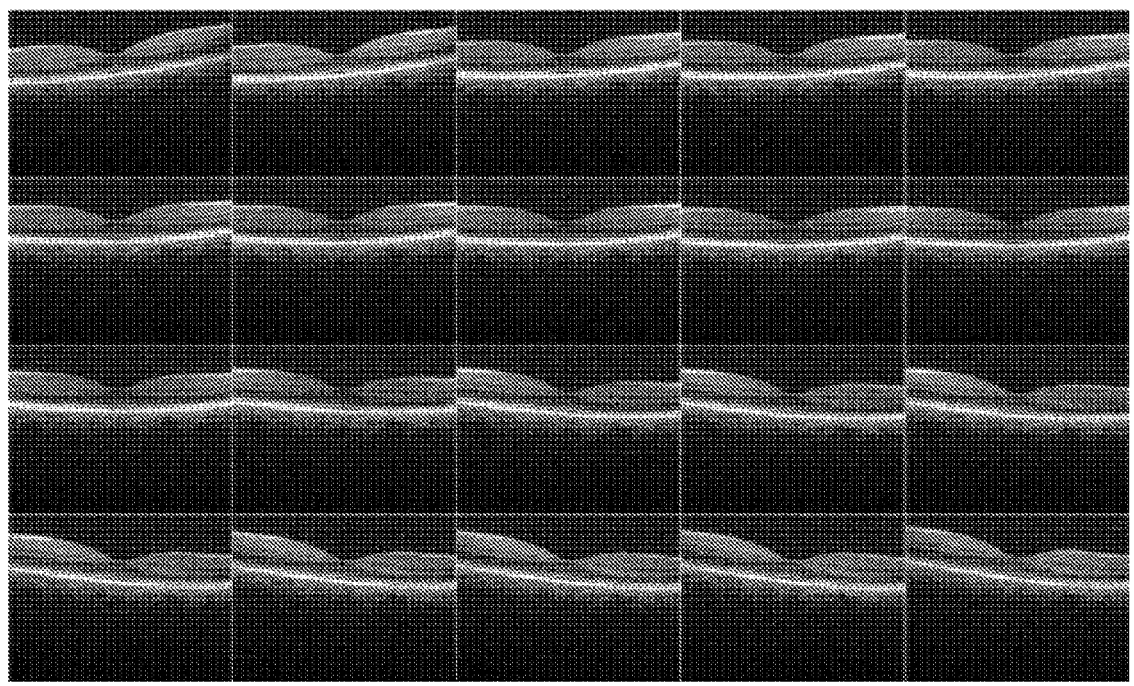
FIG. 10 shows a series of OCT images obtained over time at various different incident angles, according to embodiments of the present disclosure.

For example, FIG. 9 shows a series of OCT images obtained over time (1 second) at various different incident angles using an OCT system that included an optically reflective element. FIG. 10 shows a series of OCT images obtained over time (1 second) at various different angles, where the apparent angle of the retina ranged from ±10°. The system included an optically reflective element, which was rotated ±2.3° to obtain the series of images.

In certain embodiments, analyzing the image data includes comparing a first image produced at a first incident angle with a second image produced at a second incident angle to produce a composite image. A composite image may include image data from one or more images that are combined together into a single image, such as, but not limited to, a difference map, an integration image, and the like. For example, images from two or more different incident angles may be analyzed to produce a difference map. The difference map may include areas in which differences in the images obtained at different incident angles are highlighted (e.g., using different colors and/or intensities). In certain embodiments, the composite image includes the addition of components from images obtained at various different incident angles. In other embodiments, the composite image includes the subtraction of components from images obtained at various different incident angles.

Figure 12:
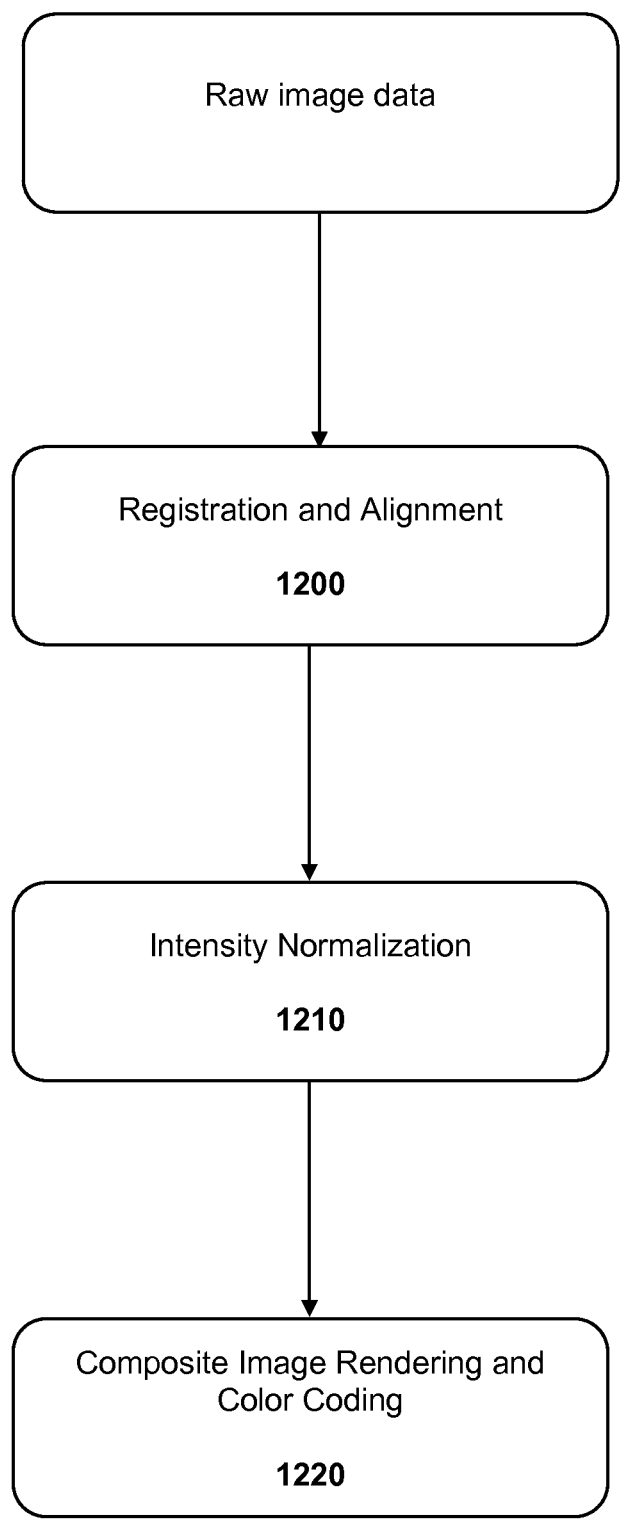
FIG. 12 shows a flow diagram of a processing algorithm used to process OCT image data, according to embodiments of the present disclosure.

In certain embodiments, the method includes processing the acquired raw data according to an analysis and interpretation algorithm. In some cases, the algorithm uses as input the directional reflectivity raw data captured using the subject directional OCT systems and methods. In certain instances, the algorithm includes programming configured to control a processor to perform one or more of the following tasks: (1) normalization of image intensity; (2) registration of images obtained at different rotational positions of the optical element; (3) measuring anatomical features in cross-sectional and/or volumetric images based on contrast-enhanced visualization; (4) analysis of the regions of change between registered images and difference mapping (e.g., by producing a false color map); (5) analysis of the regions of change between registered images and combining image data obtained at multiple rotational positions of the optical element and rendering of this composite image; and (6) analysis and interpretation of the difference between the observed directional reflectivity and the expected directional reflectivity based on the incident angle of light. For example, a flow diagram of an embodiment of a processing algorithm is shown in FIG. 12. In FIG. 12, the image data is initially processed by registration and alignment 1200, followed by intensity normalization 1210, and then composite image rendering and color coding 1220. Each of these steps is described in more detail below.

In certain embodiments, the method includes registering the images obtained at the different rotational positions of the optical element. By "registration", "registering", "alignment" or "aligning" is meant a process of transforming different sets of data into one coordinate system. For example, data may be multiple sets of image data obtained at different incident angles as described above. Registering (or aligning) the images may include determining the shape or angle of one or more structures in the image. For instance, an initial image of a retinal area may be analyzed and the shape or angle of one or more layers in the retina may be determined. Other images of the same retinal area obtained at different incident angles may also be analyzed and the shape or angle of the corresponding layer in the retina may be determined. If the determined shapes or angles are not the same, then the image may be transformed as desired such that the shapes and angles of the retinal layers are the same. In some instances, registration of the images may facilitate producing a composite image, where two or more images may be superimposed.

Figure 13:
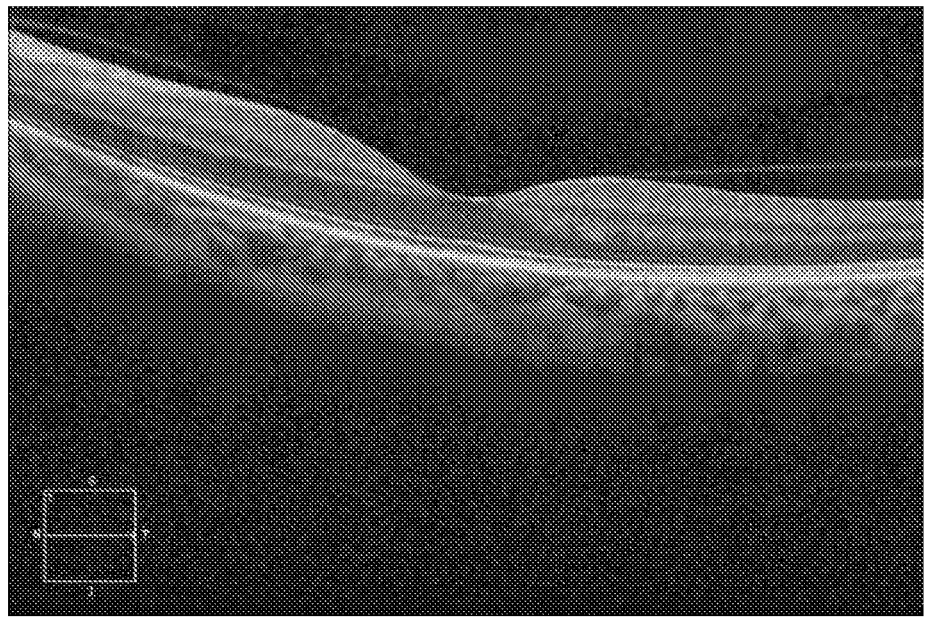
FIG. 13 shows a left inclined OCT image (FIG. 13(a)) obtained from a nasal (left) pupil position and a flat OCT image (FIG. 13(b)) before image processing, according to embodiments of the present disclosure.
Figure 13:
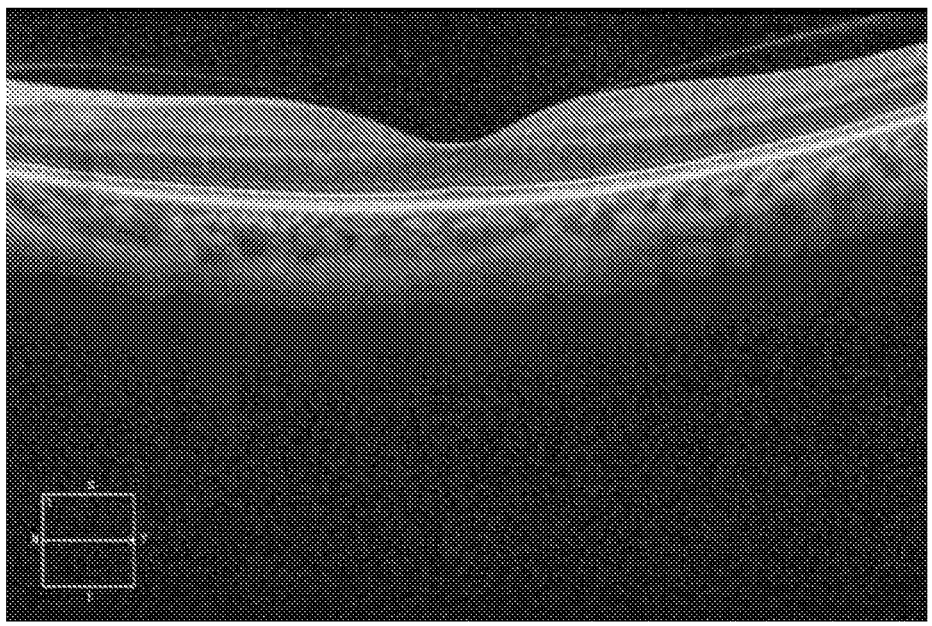

For example, FIG. 13 shows examples of retinal images as they are registered. FIG. 13(a) is a left inclined image of a retina obtained from a nasal (left) pupil position before image processing, and FIG. 13(b) is a flat image of the same retinal area obtained from a central pupil position before image processing. As described above, the shape of a layer in the retina may be determined for each image (see e.g., white lines in FIGS. 13(c) and 13(d)). As shown in FIG. 13(e), the left inclined image is transformed such that the shape and angle of the indicated retinal layer (see e.g., white line) is substantially the same as the corresponding layer in the image obtained from the central pupil position (FIG. 13(f)).

Figure 14:
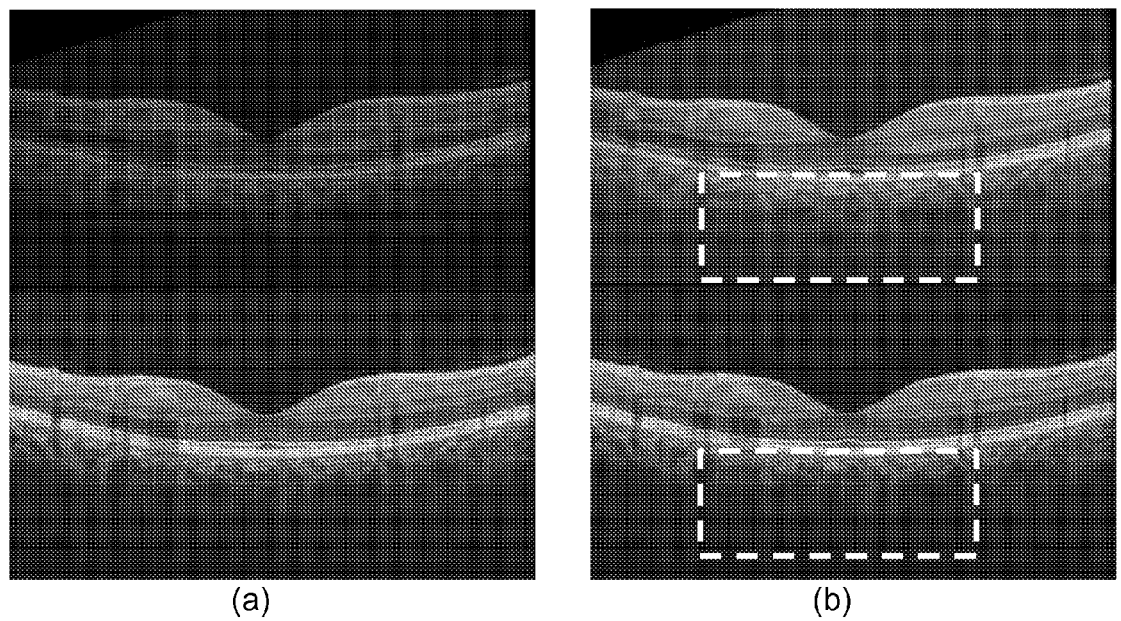
FIG. 14 shows OCT images before (FIG. 14(a)) and after (FIG. 14(b)) intensity normalization, according to embodiments of the present disclosure.

The method may further include normalizing the intensity of the image. For example, the intensity of the image may be analyzed and the intensity of the image may be adjusted (e.g., increased or decreased) as desired. When processing multiple images (such as a series of images taken at different incident angles as described above), the intensity of each image may be adjusted as desired to normalize the intensity of each image, such that the intensity of each image is substantially the same. For example, FIG. 14 shows examples of retinal images as they are processed for intensity normalization. FIG. 14(a) shows a left inclined OCT image (top) after registration and alignment. FIG. 14(b) shows a flat OCT image (bottom). As shown in FIG. 14, intensity normalization includes selecting a sample area of each image (indicated by the white boxes in FIG. 14(b)). The sample area may include non-directionally reflecting tissue (e.g., the choroid) or layers of the inner retina or vitreous. The intensity of the left inclined image (FIG. 14(b), top) is adjusted such that the intensity of the selected area is substantially the same as the intensity of the corresponding selected area in the flat OCT image (FIG. 14(b), bottom).

Figure 5:
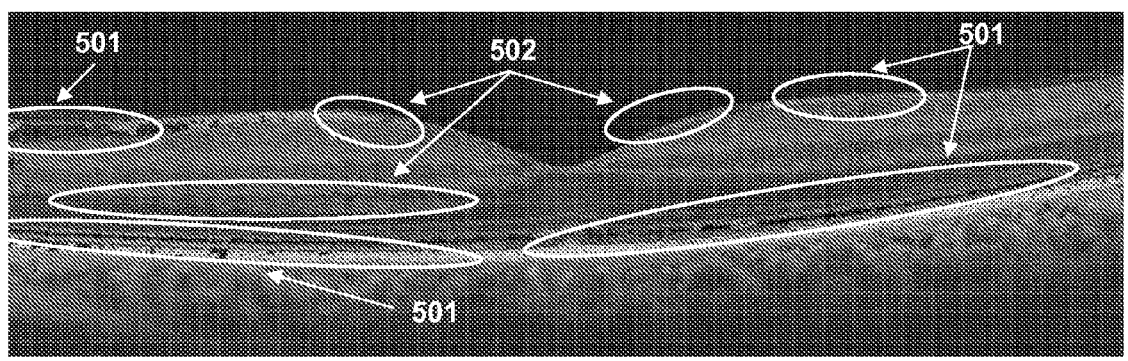
FIG. 5 shows a difference map of OCT images obtained at two different incident angles, according to embodiments of the present disclosure.
Figure 6:
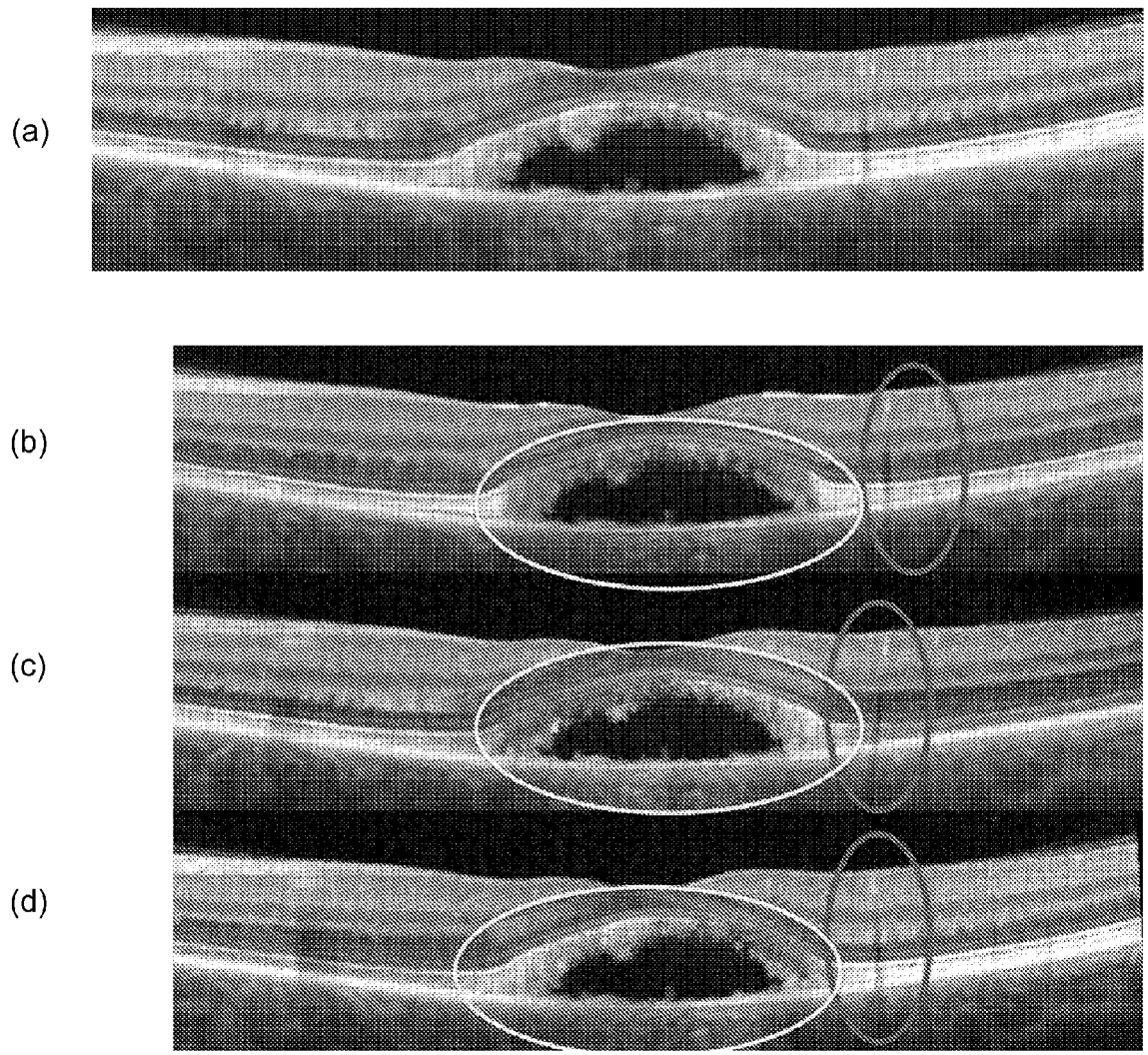
FIG. 6 shows an integration image (FIG. 6(a)) of OCT images obtained from multiple different incident angles FIGS. 6(b)-6(d), according to embodiments of the present disclosure.

In some cases, the method includes analyzing changes between registered images obtained from multiple rotational positions of the optical element and combining the images into a composite image (see e.g., FIG. 6). In certain embodiments, the method further includes analyzing changes between registered images in the composite image to produce a difference map, where differences between the registered images are visible (see e.g., FIG. 5). In some instances, one or more of the images may be color-coded, such that each image derived from a different incident angle is represented by a different color or intensity of color. Differences between the registered images may be shown by the corresponding color associated with that image from the composite image. In some cases, color coding the images may facilitate analysis of the composite image by highlighting the differences between the images that make up the composite image. In addition, color coding the images may facilitate analysis of the composite image by allowing a user to rapidly correlate the color of an image to the corresponding incident angle of that image. In certain instances, the method also includes analyzing the difference between the observed images and expected images based on incident-angle-of-light model predictions.

Figure 11:
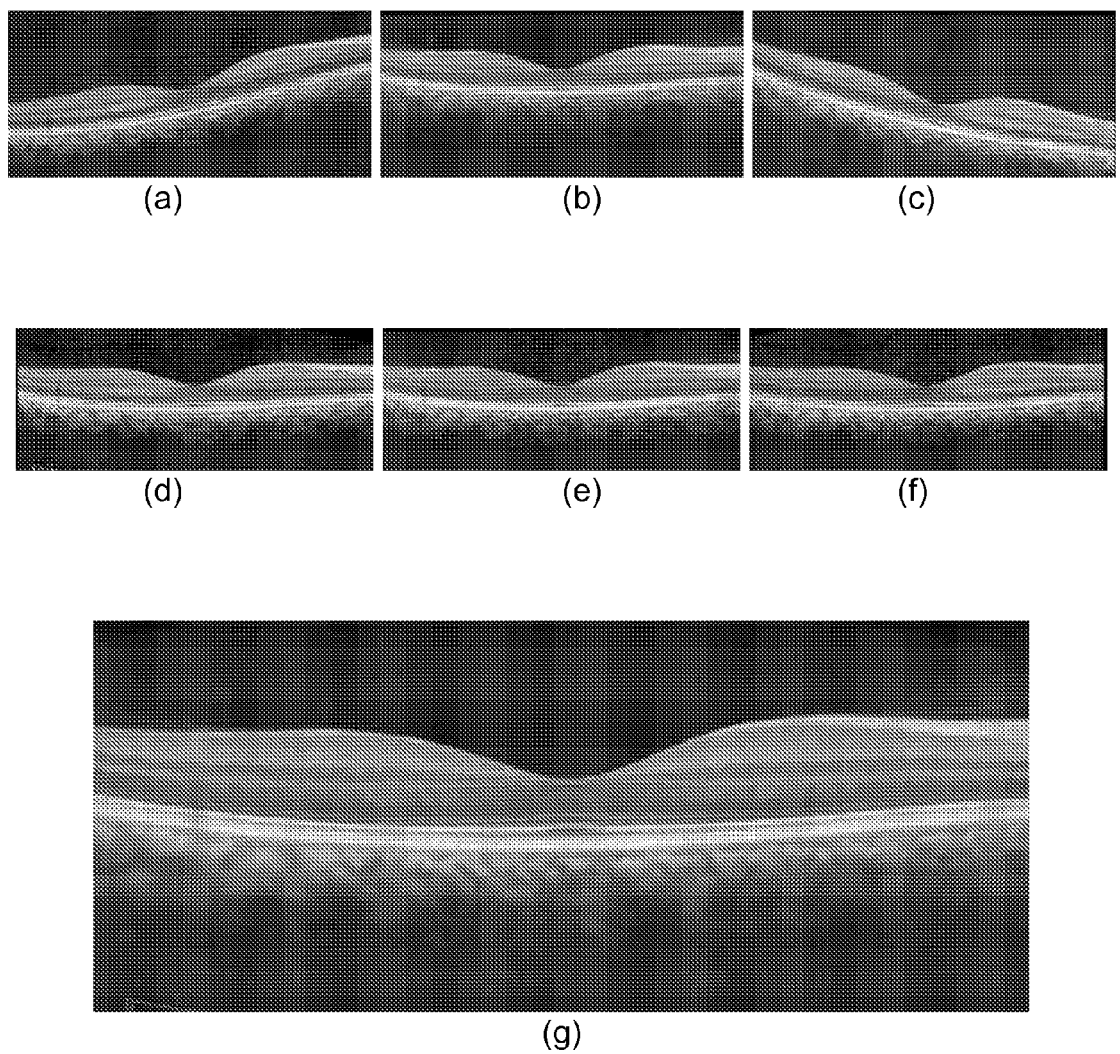
FIG. 11 shows a right inclined OCT image (FIG. 11(a)), a flat OCT image (FIG. 11(b)), and a left inclined OCT image (FIG. 11(c)) of the same retinal area, according to embodiments of the present disclosure.

For example, FIG. 11 shows a right inclined OCT image (FIG. 11(a)), a flat OCT image (FIG. 11(b)), and a left inclined OCT image (FIG. 11(c)) of the same retinal area obtained using an OCT system with an optically reflective element. FIGS. 11(d)-(f) show the same OCT images after registration and alignment. FIG. 11(g) shows a composite color coded image of FIGS. 11(d)-(f) (color not shown).

Utility

Optical coherence tomography (OCT) systems and devices as disclosed herein find use in a variety of different applications. For example, the subject systems and devices find use in visualizing and diagnosing diseases in optical tissue. A system configured to direct the OCT beam to acquire images from multiple pupil entry points may facilitate imaging of optical tissue properties and aid in the interpretation of OCT and understanding of the retina in health and disease.

In certain embodiments, the subject systems and devices find use in OCT layer studies, photoreceptor layer studies, Henle's fiber layer studies, screening for pathologies, visualization of diseased tissues, and the like.

The subject systems and devices find use in clinical and research settings. The differentiation of retinal structures may allow precise in vivo quantification of the thickness of the retinal layer (e.g., the outer nuclear layer (ONL)) indicative of photoreceptor loss in a variety of retinal diseases. The measurement of the ONL may facilitate the diagnosis and prognosis of retinal conditions in clinical care. Additionally, the ability to image the retina from various pupil entry points may facilitate visualization of existing and new classes of retinal diseases. Embodiments of the subject systems and devices may also find use in experimental and animal OCT systems.

In certain embodiments, the subject systems and devices find use in the imaging of any ocular (retinal or non-retinal) or biological tissue that have directional reflectance. In certain embodiments, the subject systems and devices are configured to acquire cross-sectional and volumetric directional reflectivity raw data and analyze the acquired data for contrast enhancement and contrast-enhanced visualization of the target tissues. The subject systems and devices may increase optical contrast and facilitate the visualization of the target (e.g., diseased) tissue. The subject systems and devices also find use in the imaging of non-retinal biological tissues that have directional reflectance. For example, the subject systems find use in the determination of refractive indices of fluids and tissues. The subject systems and devices also find use in the imaging of non-biological specimens.

In certain embodiments, directing the light (e.g., OCT beam) facilitates the acquisition of OCT images from different pupil entry points. The subject systems and devices may be incorporated into different commercial OCT systems and may facilitate the rapid acquisition of OCT images. The subject systems and devices may provide for rapid, automated scanning that may facilitate obtaining OCT images while the patient maintains fixation.

The following examples are put forth so as to provide those of ordinary skill in the art with a complete disclosure and description of how to make and use the embodiments disclosed herein, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Averages are calculated as the statistical mean average.

EXAMPLES

Example 1

Figure 15:
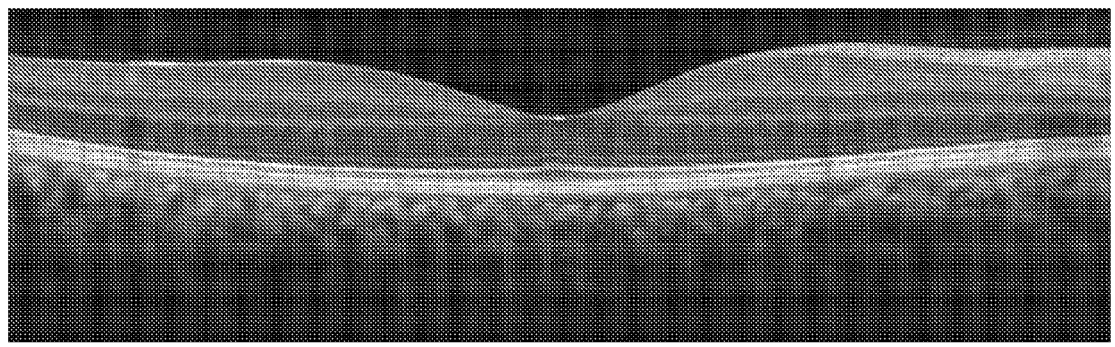
FIG. 15 shows a right inclined OCT image (FIG. 15(a)), a center OCT image (FIG. 15(b)), and a left inclined OCT image (FIG. 15(c)) of a normal retina after registration and intensity normalization, according to embodiments of the present disclosure.
Figure 15:
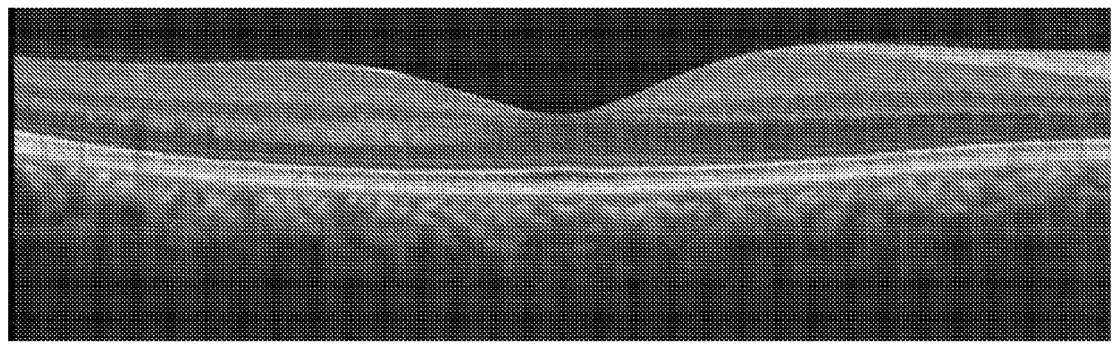
Figure 15:
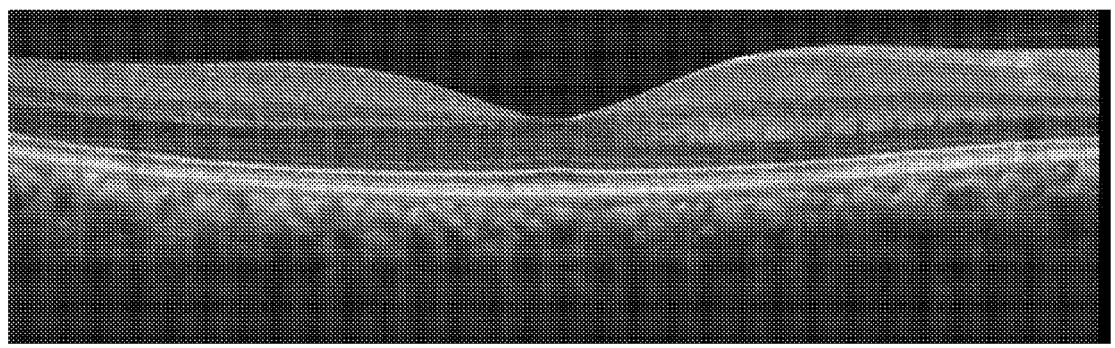

FIGS. 15(a)-(c) show OCT images of a normal retina after registration and intensity normalization; right inclined image (FIG. 15(a)), flat image (FIG. 15(b)), and left inclined image (FIG. 15(c)). FIG. 15(d) shows a composite image of FIGS. 15(a)-(c) after color coding. As shown in FIG. 15(d), directionally reflective Henle's fiber layer 1510 is indicated in red and green (colors not shown), and photoreceptor hyper-reflective bands 1520 are indicated in blue (color not shown).

Figure 16:
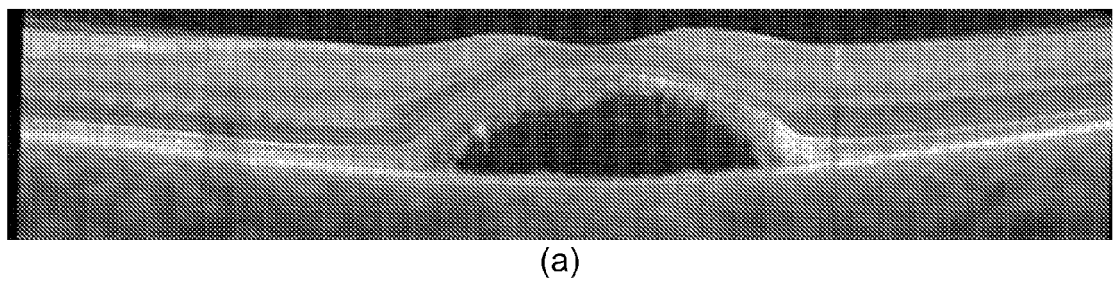
FIG. 16 shows a right inclined OCT image (FIG. 16(a)), a center OCT image (FIG. 16(b)), and a left inclined OCT image (FIG. 16(c)) of a pathological retina after registration and intensity normalization, according to embodiments of the present disclosure.
Figure 16:
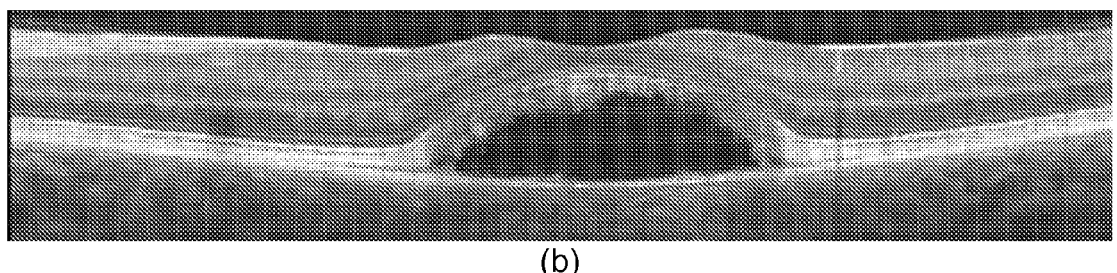
Figure 16:
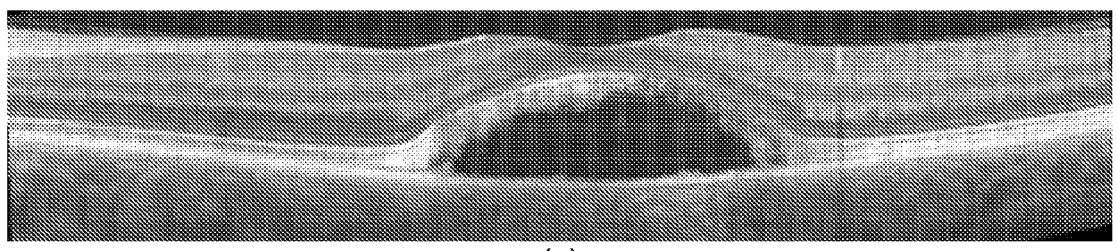

FIGS. 16(a)-(c) show OCT images of a pathological retina with Best Vitelliform Dystrophy after registration and intensity normalization; right inclined image (FIG. 16(a)), flat image (FIG. 16(b)), and left inclined image (FIG. 16(c)). FIG. 16(d) shows a composite image of FIGS. 16(a)-(c) after color coding. As shown in FIG. 16(d), directionally reflective Henle's fiber layer 1610 is indicated in red and green (colors not shown), and photoreceptor inner segment/outer segment and outer segment/retinal pigment epithelial 1620 are indicated in red, green and blue (color not shown). Thickened subretinal outer segments 1640 and subretinal material 1630 are also shown that include varying intensities of red, green and blue (color not shown).

Example 2

FIG. 5 shows a difference map of OCT images obtained at two different incident angles using an OCT system that includes an optically transmissive element. Differences between the two OCT images were calculated and displayed using a rendered false color map (color not shown). In FIG. 5, the differences are indicated by the circled areas at 501 and 502.

FIG. 6 shows a composite image (FIG. 6(a)) of images obtained from multiple incident angles (FIGS. 6(b)-6(d)) obtained using an OCT system with an optically transmissive element.

Typical OCT systems provide images of the anatomical structure of ophthalmic tissue based on its reflectance properties as imaged from a single pupil entry position. This entry position serves as a pivot point for the beam to be scanned back and forth along a single arc. The Examples above indicate that embodiments of the present disclosure that include an adjustable optical element configured to displace a pupil entry point of the light facilitated the identification of the boundary between the anatomical layer containing the photoreceptor nuclei (outer nuclear layer) and their axons (Henle's fiber layer). In certain instances, as the angle of the incident light (e.g., the OCT beam) relative to the retina was altered, contrast between these layers was enhanced because of the directional reflectivity properties of Henle's fiber layer. In cases of pathology, visualization of certain directionally reflective layers (e.g., signals from photoreceptors) may be facilitated as the angle of the OCT beam relative to the retina is adjusted.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An optical coherence tomography system comprising:
   (a) a light source;
   (b) an objective lens configured to direct light from the light source along an optical axis; and
   (c) an optical device comprising:
      i. an adjustable optical element configured to displace a pupil entry point of the light; and
      ii. a mechanism operatively coupled to the optical element and configured to rotate the optical element about one or more axes of rotation.

2. The system of claim 1, wherein the optical element is positioned between the light source and the objective lens.

3. The system of claim 1, wherein the optical element is positioned such that light passes through the objective lens before contacting the optical element.

4. The system of claim 1, wherein the optical element comprises an optically reflective element.

5. The system of claim 1, wherein the optical element comprises an optically transmissive element.

6. The system of claim 1, further comprising a scanner positioned between the light source and the objective lens and configured to scan the light from the light source in at least one dimension.

7. The system of claim 1, further comprising a photodetector configured to detect light and generate data from the detected light, and a processor configured to analyze the data to produce an image.

8. The system of claim 1, wherein the light from the light source is directed to a location on a retina of a subject and the optical element is configured to displace the optical axis of the light in an x-direction or a y-direction while directing the light to the location on the retina of the subject.

9. The system of claim 8, wherein the light directed to the location on the retina along the displaced optical axis contacts the location on the retina at a different incident angle.

10. An optical device for an optical coherence tomography system, the optical device comprising:
    (a) an adjustable optical element configured to displace a pupil entry point of light;
    (b) a mechanism operatively coupled to the optical element and configured to rotate the optical element about one or more axes of rotation; and
    (c) an attachment element configured to attach the optical device to an optical coherence tomography system.

11. The optical device of claim 10, wherein the mechanism is configured to adjust the position of the optical element while the system displays an apparently unchanged internal fixation target to the subject.

12. The optical device of claim 10, wherein light is directed to a location on a retina of a subject and the optical element is configured to displace an optical axis of the light in an x-direction or a y-direction while directing the light to the location on the retina of the subject.

13. The optical device of claim 12, wherein the light directed to the location on the retina along the displaced optical axis contacts the location on the retina at a different incident angle.

14. An optical coherence tomography method comprising:
    transmitting light from a light source towards a subject along an optical axis, wherein the light is transmitted through an optical device comprising an adjustable optical element configured to displace a pupil entry point of the light, and wherein the light contacts a sample area of the subject at an incident angle.

15. The method of claim 14, further comprising adjusting the incident angle by rotating the optical element about one or more axes of rotation.

16. The method of claim 15, wherein the light contacting the sample area of the subject illuminates a field of view on the sample area and the adjusting maintains substantially the same field of view.

17. The method of claim 15, wherein rotating the optical element displaces the optical axis of the light in an x-direction or a y-direction while contacting the light to the sample area of the subject at a different incident angle.

18. The method of claim 14, further comprising detecting light reflected by the sample area using a photodetector configured to generate data corresponding to the detected light, and analyzing the data at one or more incident angles to produce an image of the sample area.

19. The method of claim 18, wherein the analyzing comprises:
    registration and normalization of the images; and
    comparing a first image produced at a first incident angle with one or more images produced at one or more corresponding incident angles to produce one or more composite images.

20. The method of claim 19, further comprising color coding the composite image based on the contributions from different incident angles of the light.

* * * * *